United States Patent
Johnston et al.

(10) Patent No.: US 11,285,306 B2
(45) Date of Patent: Mar. 29, 2022

(54) TRANSDERMAL DRUG DELIVERY DEVICES AND METHODS

(71) Applicant: Morningside Venture Investments Limited, Newton Centre, MA (US)

(72) Inventors: Andrew L. Johnston, Redwood City, CA (US); Michael P. Schaller, Louisville, CO (US); Bryce Peterson, Redwood City, CA (US); Kevin Gelston, Moraga, CA (US)

(73) Assignee: Morningside Venture Investments Limited, Newton Centre, MA (US)

(*) Notice: Subject to any disclaimer, the term of this patent is extended or adjusted under 35 U.S.C. 154(b) by 208 days.

(21) Appl. No.: 16/473,981

(22) PCT Filed: Jan. 5, 2018

(86) PCT No.: PCT/US2018/012568
§ 371 (c)(1),
(2) Date: Jun. 26, 2019

(87) PCT Pub. No.: WO2018/129304
PCT Pub. Date: Jul. 12, 2018

(65) Prior Publication Data
US 2019/0336738 A1 Nov. 7, 2019

Related U.S. Application Data

(60) Provisional application No. 62/443,421, filed on Jan. 6, 2017.

(51) Int. Cl.
*A61M 35/00* (2006.01)
*A61K 9/70* (2006.01)
(Continued)

(52) U.S. Cl.
CPC ............. *A61M 35/00* (2013.01); *A61K 9/703* (2013.01); *A61M 5/145* (2013.01);
(Continued)

(58) Field of Classification Search
CPC ............. A61M 35/00; A61M 2205/103; A61M 2005/14268; A61M 2005/14533;
(Continued)

(56) References Cited

U.S. PATENT DOCUMENTS 2,183,482 A 12/1939 Kurkjian
3,279,653 A 10/1966 Pfleger
(Continued)

FOREIGN PATENT DOCUMENTS

AU 662877 B3 9/1995
BE 899037 A 6/1984
(Continued)

OTHER PUBLICATIONS

Abood et al.; Structure-activity studies of carbamate and other esters: agonists and antagonists to nicotine; Pharmacology Biochemistry and Behavior; 30(2); pp. 403-408; Jun. 1988.
(Continued)

*Primary Examiner* — Nicholas J. Weiss
*Assistant Examiner* — Seth Han
(74) *Attorney, Agent, or Firm* — Shay Glenn LLP

(57) ABSTRACT

A transdermal drug delivery device includes a reservoir, a transdermal membrane, a piston, a control rod, a spring, and a rotational cam. The reservoir is configured to hold a formulation. The transdermal membrane is configured to allow the formulation from the reservoir to pass therethrough. The piston is configured to move into the reservoir. The control rod is attached to the piston and includes a plurality of teeth thereon. The spring is configured to apply force to the control rod in the direction of the reservoir. The
(Continued)

rotational cam has a first camming surface and a second camming surface that are configured to engage with the plurality of teeth. The rotational cam, when rotated, is configured to disengage the first camming surface from a first tooth of the plurality of teeth, thereby allowing the spring to advance the piston into the reservoir to expel the formulation onto the transdermal membrane.

17 Claims, 11 Drawing Sheets

(51) Int. Cl.
*A61M 5/142* (2006.01)
*A61M 5/145* (2006.01)

(52) U.S. Cl.
CPC ...... *A61M 5/1454* (2013.01); *A61M 5/14248* (2013.01); *A61M 2005/14268* (2013.01); *A61M 2005/14533* (2013.01); *A61M 2205/103* (2013.01); *A61M 2205/106* (2013.01); *A61M 2205/502* (2013.01); *A61M 2205/8206* (2013.01)

(58) Field of Classification Search
CPC ........ A61M 2005/14506; A61M 5/142; A61M 5/145; A61M 5/1454; A61K 9/703; A61K 9/2054; A61K 9/2059; A61P 25/34
See application file for complete search history.

(56) References Cited

U.S. PATENT DOCUMENTS 3,845,217 A 10/1974 Ferno et al.
4,313,439 A * 2/1982 Babb .................... A61M 5/172 604/28
4,321,387 A 3/1982 Chavdarian et al.
4,327,725 A 5/1982 Cortese et al.
4,332,945 A 6/1982 Edwards
4,379,454 A 4/1983 Campbell et al.
4,545,990 A 10/1985 Le Foyer de Costil et al.
4,579,858 A 4/1986 Ferno et al.
4,590,278 A 5/1986 Edwards
4,708,716 A 11/1987 Sibalis
4,772,263 A 9/1988 Dorman et al.
4,806,356 A 2/1989 Shaw
4,853,854 A 8/1989 Behar et al.
4,885,154 A 12/1989 Cormier et al.
4,908,213 A 3/1990 Govil et al.
4,917,676 A 4/1990 Heiber et al.
4,917,895 A 4/1990 Lee et al.
4,920,989 A 5/1990 Rose et al.
4,952,928 A 8/1990 Carroll et al.
4,953,572 A 9/1990 Rose et al.
4,992,445 A 2/1991 Lawter et al.
5,000,956 A 3/1991 Amkraut et al.
5,001,139 A 3/1991 Lawter et al.
5,013,293 A 5/1991 Sibalis
5,023,252 A 6/1991 Hseih
5,049,387 A 9/1991 Amkraut
5,069,904 A 12/1991 Masterson
5,073,380 A 12/1991 Babu et al.
5,097,834 A 3/1992 Skrabal
5,120,545 A 6/1992 Ledger et al.
5,130,139 A 7/1992 Cormier et al.
5,149,538 A 9/1992 Granger et al.
5,149,719 A 9/1992 Ferber et al.
5,212,188 A 5/1993 Caldwell et al.
5,221,254 A 6/1993 Phipps
5,227,391 A 7/1993 Caldwell et al.
5,232,704 A 8/1993 Franz et al.
5,232,933 A 8/1993 Lippiello et al.
5,236,714 A 8/1993 Lee et al.
5,242,934 A 9/1993 Lippiello et al.
5,242,935 A 9/1993 Lippiello et al.
5,242,941 A 9/1993 Lewy et al.
5,248,690 A 9/1993 Caldwel et al.
5,252,604 A 10/1993 Nagv et al.
5,262,165 A 11/1993 Govil et al.
5,273,755 A 12/1993 Venkatraman et al.
5,273,756 A 12/1993 Fallon et al.
5,304,739 A 4/1994 Klug et al.
5,352,456 A 10/1994 Fallon et al.
5,364,630 A 11/1994 Osborne et al.
5,370,635 A 12/1994 Strausak et al.
5,388,571 A 2/1995 Roberts et al.
5,389,679 A 2/1995 Alliger
5,393,526 A 2/1995 Castro
5,405,614 A 4/1995 D'Angelo et al.
5,415,629 A 5/1995 Henley
5,445,609 A 8/1995 Lattin et al.
5,451,407 A 9/1995 Cormier et al.
5,464,387 A 11/1995 Haak et al.
5,472,946 A 12/1995 Peck et al.
5,501,697 A 3/1996 Fisher
5,505,958 A 4/1996 Bello et al.
5,512,306 A 4/1996 Carlsson et al.
5,516,793 A 5/1996 Duffy
5,525,351 A 6/1996 Dam
5,545,407 A 8/1996 Hall et al.
5,562,607 A 10/1996 Gyory
5,596,994 A 1/1997 Bro
5,601,839 A 2/1997 Quan et al.
5,616,332 A 4/1997 Herstein
5,618,557 A 4/1997 Wille et al.
5,653,682 A 8/1997 Sibalis
5,656,255 A 8/1997 Jones
5,662,920 A 9/1997 Santus
5,686,100 A 11/1997 Wille et al.
5,688,232 A 11/1997 Flower
5,697,896 A 12/1997 McNichols et al.
5,716,987 A 2/1998 Wille
5,722,418 A 3/1998 Bro
5,733,259 A 3/1998 Valcke et al.
5,785,688 A 7/1998 Joshi et al.
5,797,867 A 8/1998 Guerrera et al.
5,820,875 A 10/1998 Fallon et al.
5,833,466 A 11/1998 Borg
5,843,979 A 12/1998 Wille et al.
5,846,559 A 12/1998 Hopp
5,865,786 A 2/1999 Sibalis et al.
5,876,368 A 3/1999 Flower
5,879,292 A 3/1999 Sternberg et al.
5,879,322 A 3/1999 Lattin et al.
5,882,676 A 3/1999 Lee et al.
5,908,301 A 6/1999 Lutz
5,919,156 A 7/1999 Stropkay et al.
5,932,240 A 8/1999 D'Angelo et al.
5,945,123 A 8/1999 Hermelin
5,967,789 A 10/1999 Segel et al.
5,972,389 A 10/1999 Shell et al.
5,993,435 A 11/1999 Haak et al.
5,997,501 A 12/1999 Gross et al.
6,018,679 A 1/2000 Dinh et al.
6,019,997 A 2/2000 Scholz et al.
6,024,981 A 2/2000 Khankari et al.
6,034,079 A 3/2000 Sanberg et al.
6,059,736 A 5/2000 Tapper
6,059,753 A 5/2000 Faust et al.
6,068,853 A 5/2000 Giannos et al.
6,081,734 A 6/2000 Batz
6,090,404 A 7/2000 Meconi et al.
6,093,419 A 7/2000 Rolf
6,120,803 A 9/2000 Wong et al.
6,129,702 A 10/2000 Woias et al.
6,165,155 A 12/2000 Jacobsen et al.
6,211,194 B1 4/2001 Westman et al.
6,211,296 B1 4/2001 Frate et al.
6,221,394 B1 4/2001 Gilbert et al.
6,238,689 B1 5/2001 Rhodes et al.
6,274,606 B1 8/2001 Caldwell et al.
6,310,102 B1 10/2001 Dull et al.
6,365,182 B1 4/2002 Khankari et al.

(56) References Cited

U.S. PATENT DOCUMENTS

| | | |
|---|---|---|
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |
| 6,436,078 B1 | 8/2002 | Svedman |
| 6,437,004 B1 | 8/2002 | Perricone |
| 6,454,708 B1 | 9/2002 | Ferguson et al. |
| 6,488,959 B2 | 12/2002 | Stanley et al. |
| 6,492,399 B1 | 12/2002 | Dull et al. |
| 6,539,250 B1 | 3/2003 | Bettinger |
| 6,546,281 B1 | 4/2003 | Zhang et al. |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,011,849 B2 | 3/2006 | Storm et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,931,563 B2 | 4/2011 | Shaw et al. |
| 7,988,660 B2 | 8/2011 | Byland et al. |
| 8,003,080 B2 | 8/2011 | Rabinowitz et al. |
| 8,021,334 B2 | 9/2011 | Shekalim |
| 8,137,314 B2 | 3/2012 | Mounce et al. |
| 8,140,143 B2 | 3/2012 | Picard et al. |
| 8,192,756 B2 | 6/2012 | Berner et al. |
| 8,246,581 B2 | 8/2012 | Adams et al. |
| 8,252,321 B2 | 8/2012 | DiPierro et al. |
| 8,262,394 B2 | 9/2012 | Walker et al. |
| 8,268,475 B2 | 9/2012 | Tucholski |
| 8,285,328 B2 | 10/2012 | Caffey et al. |
| 8,303,500 B2 | 11/2012 | Raheman |
| 8,309,568 B2 | 11/2012 | Stinchcomb et al. |
| 8,372,040 B2 | 2/2013 | Huang et al. |
| 8,414,532 B2 | 4/2013 | Brandt et al. |
| 8,440,220 B2 | 5/2013 | Gale et al. |
| 8,440,221 B2 | 5/2013 | Zumbrunn et al. |
| 8,441,411 B2 | 5/2013 | Tucholski et al. |
| 8,445,010 B2 | 5/2013 | Anderson et al. |
| 8,449,471 B2 | 5/2013 | Tran |
| 8,517,988 B2 | 8/2013 | Smith |
| 8,545,445 B2 | 10/2013 | Kamen et al. |
| 8,574,188 B2 | 11/2013 | Potter et al. |
| 8,586,079 B2 | 11/2013 | Hansted et al. |
| 8,589,174 B2 | 11/2013 | Nelson et al. |
| 8,614,278 B2 | 12/2013 | Loubert et al. |
| 8,632,497 B2 | 1/2014 | Yodfat et al. |
| 8,666,781 B2 | 3/2014 | Hanina et al. |
| 8,673,346 B2 | 3/2014 | Zumbrunn et al. |
| 8,684,922 B2 | 4/2014 | Tran |
| 8,688,189 B2 | 4/2014 | Shennib |
| 8,690,827 B2 | 4/2014 | Edwards et al. |
| 8,690,865 B2 | 4/2014 | Prausnitz et al. |
| 8,696,637 B2 | 4/2014 | Ross |
| 8,703,175 B2 | 4/2014 | Kanios et al. |
| 8,703,177 B2 | 4/2014 | Finn et al. |
| 8,722,233 B2 | 5/2014 | Tucholski |
| 8,727,745 B2 | 5/2014 | Rush et al. |
| 8,741,336 B2 | 6/2014 | DiPierro et al. |
| 8,747,348 B2 | 6/2014 | Yodfat et al. |
| 8,753,315 B2 | 6/2014 | Alfemess et al. |
| 8,773,257 B2 | 7/2014 | Yodfat et al. |
| 8,814,822 B2 | 8/2014 | Yodfat et al. |
| 8,862,223 B2 | 10/2014 | Yanaki |
| 8,864,727 B2 | 10/2014 | Lee |
| 8,865,207 B2 | 10/2014 | Kanios et al. |
| 8,872,663 B2 | 10/2014 | Forster |
| 8,876,802 B2 | 11/2014 | Grigorov |
| 8,956,644 B2 | 2/2015 | Yum et al. |
| 8,962,014 B2 | 2/2015 | Prinz et al. |
| 8,986,253 B2 | 3/2015 | DiPerna |
| 8,999,356 B1 | 4/2015 | Ramirez et al. |
| 8,999,372 B2 | 4/2015 | Davidson et al. |
| 9,023,392 B2 | 5/2015 | Koo et al. |
| 9,044,582 B2 | 6/2015 | Chang et al. |
| 9,050,348 B2 | 6/2015 | Kydonieus et al. |
| 9,078,833 B2 | 7/2015 | Audett |
| 9,111,085 B1 | 8/2015 | Darmour et al. |
| 9,114,240 B2 | 8/2015 | Horstmann et al. |
| 9,155,712 B2 | 10/2015 | Kanios et al. |
| 9,233,203 B2 | 1/2016 | Moberg et al. |
| 9,238,001 B2 | 1/2016 | Weyer et al. |
| 9,238,108 B2 | 1/2016 | Edwards et al. |
| 9,248,104 B2 | 2/2016 | Valia et al. |
| 9,289,397 B2 | 3/2016 | Wright |
| 9,308,202 B2 | 4/2016 | Hille et al. |
| 9,314,527 B2 | 4/2016 | Cottrell et al. |
| 9,373,269 B2 | 6/2016 | Bergman et al. |
| 9,380,698 B1 | 6/2016 | Li et al. |
| RE46,217 E | 11/2016 | Huang et al. |
| 9,513,666 B2 | 12/2016 | Li et al. |
| 9,549,903 B2 | 1/2017 | Hille et al. |
| 9,555,226 B2 | 1/2017 | Zumbrunn et al. |
| 9,555,227 B2 | 1/2017 | DiPierro |
| 9,555,277 B2 | 1/2017 | Yeh |
| 9,623,017 B2 | 4/2017 | Barbier et al. |
| 9,636,457 B2 | 5/2017 | Newberry et al. |
| 9,655,843 B2 | 5/2017 | Finn et al. |
| 9,656,441 B2 | 5/2017 | LeDonne et al. |
| 9,669,199 B2 | 6/2017 | DiPierro et al. |
| 9,687,186 B2 | 6/2017 | Goldstein et al. |
| 9,693,689 B2 | 7/2017 | Gannon et al. |
| 9,700,552 B2 | 7/2017 | Weimann |
| 9,717,698 B2 | 8/2017 | Horstmann et al. |
| 9,735,893 B1 | 8/2017 | Aleksov et al. |
| 9,782,082 B2 | 10/2017 | Gannon et al. |
| 9,795,681 B2 | 10/2017 | Abreu |
| 9,867,539 B2 | 1/2018 | Heikenfeld et al. |
| 9,895,320 B2 | 2/2018 | Ogino et al. |
| 9,949,935 B2 | 4/2018 | Murata |
| 9,974,492 B1 | 5/2018 | Dicks et al. |
| 9,993,203 B2 | 6/2018 | Mei et al. |
| 10,004,447 B2 | 6/2018 | Shen et al. |
| 10,034,841 B2 | 7/2018 | Müller et al. |
| 10,105,487 B2 | 10/2018 | DiPierro et al. |
| 10,143,687 B2 | 12/2018 | Azhir |
| 10,213,586 B2 | 2/2019 | Netzel et al. |
| 10,232,156 B2 | 3/2019 | Netzel et al. |
| 10,258,738 B2 | 4/2019 | Dipierro et al. |
| 10,258,778 B2 | 4/2019 | DiPierro et al. |
| 10,679,516 B2 | 6/2020 | Darmour et al. |

(56) References Cited

U.S. PATENT DOCUMENTS

| | | |
|---|---|---|
| 10,716,764 B2 | 7/2020 | Zumbrunn et al. |
| 2001/0022978 A1 | 9/2001 | Lacharriere et al. |
| 2001/0026788 A1 | 10/2001 | Piskorz |
| 2002/0002189 A1 | 1/2002 | Smith et al. |
| 2002/0034535 A1 | 3/2002 | Kleiner et al. |
| 2002/0106329 A1 | 8/2002 | Leslie |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Cretan |
| 2003/0004187 A1 | 1/2003 | Bedard et al. |
| 2003/0065294 A1 | 4/2003 | Pickup et al. |
| 2003/0065924 A1 | 4/2003 | Wuidart et al. |
| 2003/0083645 A1 | 5/2003 | Angel et al. |
| 2003/0087937 A1 | 5/2003 | Lindberg |
| 2003/0119879 A1 | 6/2003 | Landh et al. |
| 2003/0159702 A1 | 8/2003 | Lindell et al. |
| 2004/0019321 A1 | 1/2004 | Sage et al. |
| 2004/0034068 A1 | 2/2004 | Warchol et al. |
| 2004/0037879 A1 | 2/2004 | Adusumilli et al. |
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0219192 A1 | 11/2004 | Horstmann et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2005/0197625 A1* | 9/2005 | Haueter .............. A61M 5/1454 604/131 |
| 2005/0266032 A1 | 12/2005 | Srinivasan et al. |
| 2005/0276852 A1 | 12/2005 | Davis et al. |
| 2006/0024358 A1 | 2/2006 | Santini et al. |
| 2006/0036209 A1 | 2/2006 | Subramony et al. |
| 2006/0057202 A1 | 3/2006 | Antarkar et al. |
| 2006/0122577 A1 | 6/2006 | Poulsen et al. |
| 2006/0167039 A1 | 7/2006 | Nguyen et al. |
| 2006/0184093 A1 | 8/2006 | Phipps et al. |
| 2006/0188859 A1 | 8/2006 | Yakobi |
| 2006/0204578 A1 | 9/2006 | Vergez et al. |
| 2006/0206054 A1 | 9/2006 | Shekalim |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0104787 A1 | 5/2007 | Posey Dowty et al. |
| 2007/0149952 A1 | 6/2007 | Biand et al. |
| 2007/0154336 A1 | 7/2007 | Miyazaki et al. |
| 2007/0168501 A1 | 7/2007 | Cobb et al. |
| 2007/0179172 A1 | 8/2007 | Becker et al. |
| 2007/0191815 A1 | 8/2007 | DiPierro |
| 2007/0250018 A1 | 10/2007 | Adachi et al. |
| 2007/0256684 A1 | 11/2007 | Kelliher et al. |
| 2007/0260491 A1 | 11/2007 | Palmer et al. |
| 2007/0279217 A1 | 12/2007 | Venkatraman et al. |
| 2007/0299401 A1 | 12/2007 | Alfemess et al. |
| 2008/0008747 A1 | 1/2008 | Royds |
| 2008/0131494 A1 | 6/2008 | Reed et al. |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0139907 A1 | 6/2008 | Rao et al. |
| 2008/0152592 A1 | 6/2008 | Rebec |
| 2008/0195946 A1 | 8/2008 | Peri-Glass |
| 2008/0201174 A1 | 8/2008 | Ramasubramanian et al. |
| 2008/0233178 A1 | 9/2008 | Reidenberg et al. |
| 2008/0274168 A1 | 11/2008 | Baker et al. |
| 2008/0319272 A1 | 12/2008 | Patangay et al. |
| 2009/0005009 A1 | 1/2009 | Marsili |
| 2009/0010998 A1 | 1/2009 | Marchitto et al. |
| 2009/0024004 A1 | 1/2009 | Yang |
| 2009/0062754 A1 | 3/2009 | Tang |
| 2009/0118710 A1 | 5/2009 | Kortzeborn |
| 2009/0169631 A1 | 7/2009 | Zamloot et al. |
| 2009/0246265 A1 | 10/2009 | Stinchcomb et al. |
| 2009/0247985 A1 | 10/2009 | Melsheimer et al. |
| 2009/0259176 A1 | 10/2009 | Yairi |
| 2009/0299156 A1 | 12/2009 | Simpson et al. |
| 2010/0003653 A1 | 1/2010 | Brown |
| 2010/0068250 A1 | 3/2010 | Anderson et al. |
| 2010/0114008 A1 | 5/2010 | Marchitto et al. |
| 2010/0130932 A1 | 5/2010 | Yodfat et al. |
| 2010/0145303 A1 | 6/2010 | Yodfat et al. |
| 2010/0179473 A1 | 7/2010 | Genosar |
| 2010/0196463 A1 | 8/2010 | Quik et al. |
| 2010/0248198 A1 | 9/2010 | Seidman et al. |
| 2010/0273738 A1 | 10/2010 | Valcke et al. |
| 2010/0280432 A1 | 11/2010 | DiPierro et al. |
| 2011/0004072 A1 | 1/2011 | Fletcher et al. |
| 2011/0053129 A1 | 3/2011 | Basson et al. |
| 2011/0054285 A1 | 3/2011 | Searle et al. |
| 2011/0109439 A1 | 5/2011 | Borlenghi |
| 2011/0137255 A1 | 6/2011 | Nielsen et al. |
| 2011/0152635 A1 | 6/2011 | Morris et al. |
| 2011/0153360 A1 | 6/2011 | Hanina et al. |
| 2011/0160640 A1 | 6/2011 | Yanaki |
| 2011/0241446 A1 | 10/2011 | Tucholski |
| 2011/0245633 A1 | 10/2011 | Goldberg et al. |
| 2011/0245783 A1 | 10/2011 | Stinchcomb et al. |
| 2011/0250576 A1 | 10/2011 | Hester |
| 2011/0256517 A1 | 10/2011 | Swanson |
| 2011/0264028 A1 | 10/2011 | Ramdas et al. |
| 2011/0268809 A1 | 11/2011 | Brinkley et al. |
| 2011/0275987 A1 | 11/2011 | Caffey et al. |
| 2012/0046644 A1 | 2/2012 | Ziaie et al. |
| 2012/0078216 A1* | 3/2012 | Smith .................. A61M 5/1452 604/500 |
| 2012/0123387 A1 | 5/2012 | Gonzalez et al. |
| 2012/0156138 A1 | 6/2012 | Smith |
| 2012/0171277 A1 | 7/2012 | Royds |
| 2012/0178065 A1 | 7/2012 | Naghavi et al. |
| 2012/0203573 A1 | 8/2012 | Mayer et al. |
| 2012/0209223 A1 | 8/2012 | Salman et al. |
| 2012/0221251 A1 | 8/2012 | Rosenberg et al. |
| 2012/0244503 A1 | 9/2012 | Neveldine |
| 2012/0302844 A1 | 11/2012 | Schnidrig et al. |
| 2012/0316896 A1 | 12/2012 | Rahman et al. |
| 2012/0329017 A1 | 12/2012 | Pham |
| 2013/0017259 A1 | 1/2013 | Azhir |
| 2013/0096495 A1* | 4/2013 | Holmqvist .......... A61M 5/2066 604/89 |
| 2013/0123719 A1 | 5/2013 | Mao et al. |
| 2013/0158430 A1 | 6/2013 | Aceti et al. |
| 2013/0178826 A1 | 7/2013 | Li |
| 2013/0190683 A1 | 7/2013 | Hanson et al. |
| 2013/0216989 A1 | 8/2013 | Cuthbert |
| 2013/0253430 A1 | 9/2013 | Kouyoumjian et al. |
| 2013/0302398 A1 | 11/2013 | Ambati et al. |
| 2013/0311917 A1 | 11/2013 | Bar-or et al. |
| 2013/0317384 A1 | 11/2013 | Le |
| 2013/0328572 A1 | 12/2013 | Wang et al. |
| 2013/0345633 A1 | 12/2013 | Chong |
| 2014/0046288 A1 | 2/2014 | Geipel et al. |
| 2014/0073883 A1 | 3/2014 | Rao et al. |
| 2014/0088554 A1 | 3/2014 | Li et al. |
| 2014/0099614 A1 | 4/2014 | Hu et al. |
| 2014/0100241 A1 | 4/2014 | Slater et al. |
| 2014/0163521 A1* | 6/2014 | O'Connor .......... A61M 5/14248 604/506 |

(56) References Cited

U.S. PATENT DOCUMENTS

| | | |
|---|---|---|
| 2014/0200525 A1 | 7/2014 | DiPierro |
| 2014/0206327 A1 | 7/2014 | Ziemianska et al. |
| 2014/0207047 A1 | 7/2014 | DiPierro et al. |
| 2014/0228736 A1 | 8/2014 | Eppstein et al. |
| 2014/0237028 A1 | 8/2014 | Messenger et al. |
| 2014/0240124 A1 | 8/2014 | Bychkov |
| 2014/0266584 A1 | 9/2014 | Ingle et al. |
| 2014/0272844 A1 | 9/2014 | Hendriks et al. |
| 2014/0272845 A1 | 9/2014 | Hendriks et al. |
| 2014/0272846 A1 | 9/2014 | Richling |
| 2014/0275135 A1 | 9/2014 | Genov et al. |
| 2014/0275932 A1 | 9/2014 | Zadig |
| 2014/0276127 A1 | 9/2014 | Ferdosi et al. |
| 2014/0279740 A1 | 9/2014 | Werevi et al. |
| 2014/0302121 A1 | 10/2014 | Bevier |
| 2014/0303574 A1 | 10/2014 | Knutson |
| 2014/0365408 A1 | 12/2014 | Snyder et al. |
| 2014/0378943 A1 | 12/2014 | Geipel |
| 2015/0057616 A1 | 2/2015 | Shergold et al. |
| 2015/0209783 A1 | 7/2015 | Ingber et al. |
| 2015/0273148 A1 | 10/2015 | Sexton et al. |
| 2015/0283367 A1* | 10/2015 | Dipierro ............... A61K 9/703 604/890.1 |
| 2015/0310760 A1 | 10/2015 | Knotts et al. |
| 2015/0342900 A1 | 12/2015 | Putnins |
| 2016/0030412 A1 | 2/2016 | Azhir |
| 2016/0058939 A1 | 3/2016 | Brewer et al. |
| 2016/0220553 A1 | 8/2016 | Azhir |
| 2016/0220798 A1* | 8/2016 | Netzel ............... A61M 5/14248 |
| 2016/0227361 A1 | 8/2016 | Booth et al. |
| 2016/0228383 A1 | 8/2016 | Zhang et al. |
| 2016/0235732 A1 | 8/2016 | Quik et al. |
| 2016/0235916 A1 | 8/2016 | Edwards et al. |
| 2016/0310664 A1 | 10/2016 | McKenzie et al. |
| 2016/0317057 A1 | 11/2016 | Li et al. |
| 2016/0317738 A1* | 11/2016 | Cross ............... A61M 5/16881 |
| 2016/0339174 A1 | 11/2016 | Shapley et al. |
| 2016/0346462 A1 | 12/2016 | Adams et al. |
| 2017/0007550 A1 | 1/2017 | Enscore et al. |
| 2017/0079932 A1 | 3/2017 | Emgenbroich et al. |
| 2017/0100573 A1 | 4/2017 | DiPierro |
| 2017/0189348 A1 | 7/2017 | Lee et al. |
| 2017/0189534 A1 | 7/2017 | Lee et al. |
| 2017/0207825 A1 | 7/2017 | Belogolovy |
| 2017/0209429 A1 | 7/2017 | Stinchcomb et al. |
| 2017/0232192 A1 | 8/2017 | Sasaki |
| 2017/0249433 A1 | 8/2017 | Hagen et al. |
| 2017/0296107 A1 | 10/2017 | Reid et al. |
| 2017/0296317 A1 | 10/2017 | Gordon |
| 2017/0351840 A1 | 12/2017 | Goguen |
| 2018/0014783 A1 | 1/2018 | Shi et al. |
| 2018/0028069 A1 | 2/2018 | Shi et al. |
| 2018/0028070 A1 | 2/2018 | Shi |
| 2018/0028071 A1 | 2/2018 | Shi |
| 2018/0028072 A1 | 2/2018 | Shi |
| 2018/0110768 A1 | 4/2018 | Quik et al. |
| 2018/0110975 A1 | 4/2018 | Ivanoff et al. |
| 2018/0165566 A1 | 6/2018 | Rogers et al. |
| 2018/0168504 A1 | 6/2018 | Ding et al. |
| 2018/0197637 A1 | 7/2018 | Chowdhury |
| 2018/0374381 A1 | 12/2018 | Darmour et al. |
| 2019/0000828 A1 | 1/2019 | Azhir |
| 2019/0054078 A1 | 2/2019 | Azhir et al. |
| 2019/0054235 A1 | 2/2019 | DiPierro et al. |
| 2019/0231707 A1 | 8/2019 | Stiles et al. |
| 2019/0275308 A1 | 9/2019 | Netzel et al. |
| 2019/0374482 A1 | 12/2019 | Schaller et al. |
| 2020/0030590 A1 | 1/2020 | Buchman et al. |
| 2021/1096935 | 7/2021 | Tong et al. |

FOREIGN PATENT DOCUMENTS

| | | |
|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 311313 A2 | 4/1989 |
| EP | 0314528 B1 | 12/1992 |
| EP | 0354554 B1 | 1/1994 |
| EP | 0726005 A1 | 8/1996 |
| EP | 857725 A1 | 8/1998 |
| EP | 870768 A1 | 10/1998 |
| EP | 955301 A2 | 11/1999 |
| EP | 061252581 | 9/2001 |
| EP | 1815784 A1 | 8/2007 |
| EP | 1977746 B1 | 7/2014 |
| EP | 1662989 B1 | 9/2014 |
| EP | 3016586 A2 | 5/2016 |
| GB | 1528391 A | 10/1978 |
| GB | 2030862 A | 4/1980 |
| GB | 2142822 A | 1/1985 |
| GB | 2230439 A | 10/1990 |
| JP | 02202813 A | 8/1990 |
| JP | H09504974 A | 5/1997 |
| JP | 09512006 A | 12/1997 |
| JP | 2000515334 A | 11/2000 |
| JP | 2001505491 A | 4/2001 |
| JP | 2002092180 A | 3/2002 |
| JP | 2003506477 A | 2/2003 |
| JP | 2005521526 A | 7/2005 |
| JP | 2005525147 A | 8/2005 |
| JP | 2009544338 A | 12/2009 |
| JP | 2010518914 A | 6/2010 |
| JP | 2010279808 A | 12/2010 |
| JP | 2011036491 A | 2/2011 |
| JP | 2013524951 A | 6/2013 |
| JP | 2015070868 A | 4/2015 |
| JP | 2016202904 A | 12/2016 |
| WO | WO86/07269 A1 | 12/1986 |
| WO | WO88/003803 A1 | 6/1988 |
| WO | WO91/14441 A1 | 10/1991 |
| WO | WO92/021339 A1 | 12/1992 |
| WO | WO94/008992 A1 | 4/1994 |
| WO | WO94/010987 A1 | 5/1994 |
| WO | WO95/06497 A1 | 3/1995 |
| WO | WO96/015123 A1 | 5/1996 |
| WO | WO96/040682 A1 | 12/1996 |
| WO | WO97/011072 A1 | 3/1997 |
| WO | WO97/011073 A1 | 3/1997 |
| WO | WO97/11741 A1 | 4/1997 |
| WO | WO97/18782 A1 | 5/1997 |
| WO | WO97/019059 A1 | 5/1997 |
| WO | WO97/028801 A1 | 8/1997 |
| WO | WO97/034605 A1 | 9/1997 |
| WO | WO97/042941 A2 | 11/1997 |
| WO | WO97/046554 A1 | 12/1997 |
| WO | WO98/042713 A1 | 10/1998 |
| WO | WO98/46093 A1 | 10/1998 |
| WO | WO98/054152 A1 | 12/1998 |
| WO | WO98/054181 A1 | 12/1998 |
| WO | WO98/054182 A1 | 12/1998 |
| WO | WO98/054189 A1 | 12/1998 |
| WO | WO98/55107 A1 | 12/1998 |
| WO | WO99/002517 A1 | 1/1999 |
| WO | WO99/003859 A1 | 1/1999 |
| WO | WO99/021834 A1 | 5/1999 |
| WO | WO99/024422 A1 | 5/1999 |
| WO | WO99/066916 A1 | 12/1999 |
| WO | WO00/010997 A1 | 3/2000 |
| WO | WO00/032600 A1 | 6/2000 |
| WO | WO00/035456 A1 | 6/2000 |
| WO | WOOO/034279 A1 | 6/2000 |
| WO | WOOO/034284 A1 | 6/2000 |
| WO | WOOO/035279 A1 | 6/2000 |
| WO | WO00/034755 A1 | 8/2000 |
| WO | WO00/066596 A1 | 11/2000 |
| WO | WOOO/064885 A1 | 11/2000 |
| WO | WO00/74933 A1 | 12/2000 |
| WO | WOOO/74763 A2 | 12/2000 |
| WO | WO01/005459 A1 | 1/2001 |
| WO | WO01/037814 A1 | 5/2001 |
| WO | WO02/076211 A1 | 10/2002 |

(56) References Cited

FOREIGN PATENT DOCUMENTS

| | | |
|---|---|---|
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2007/041544 A1 | 4/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO2008/054788 A2 | 5/2008 |
| WO | WO2008/069921 A2 | 6/2008 |
| WO | WO2008/069970 A2 | 6/2008 |
| WO | WO2008/069972 A2 | 6/2008 |
| WO | WO2008/122049 A2 | 10/2008 |
| WO | WO2008/135283 A1 | 11/2008 |
| WO | WO2009/136304 A2 | 11/2009 |
| WO | WO2011/088072 A2 | 7/2011 |
| WO | WO2012/012846 A1 | 2/2012 |
| WO | WO2012/101060 A1 | 8/2012 |
| WO | WO2013/093666 A1 | 6/2013 |
| WO | WO2013/168068 A1 | 11/2013 |
| WO | WO2014/001877 A1 | 1/2014 |
| WO | WO2014/043502 A1 | 3/2014 |
| WO | WO2016/081616 A2 | 5/2016 |
| WO | WO2016/161416 A1 | 10/2016 |
| WO | WO2017/053938 A1 | 3/2017 |
| WO | WO2017/125455 A1 | 7/2017 |
| WO | WO2018/026759 A1 | 2/2018 |
| WO | WO2018/129363 A1 | 7/2018 |
| WO | WO2019/090125 A2 | 5/2019 |

OTHER PUBLICATIONS

Ahlskog et al.; Frequency of levodopa-relaled dyskinesias and motor fluctuations as estimated from the cumulative literature; Movement Disorders; 16(3); pp. 448-458; May 1, 2001.

Angulo et al.; Oral nicotine in treatment of primary sclerosing cholangitis: a pilot study; Digestive diseases and sciences; 44(3); pp. 602-607; Mar. 1, 1999.

Azhir, Arasteh; U.S. Appl. No. 62/320,871 entitled "Compositions and methods for treatment related to fail and fall frequency in neurodegenerative diseases", filed Apr. 11, 2016.

Baldessarini et al.; Preclinical studies of the pharmacology of aporphines; In: Gessa GL, Corsini GU, eds.; Apomorphine and other dopaminomi-'metics vol. 1, Basic pharmacology; New York: Raven Press; pp. 219-228; (year of pub. sufficiently earlier than effective US filing date and any foreign priority date) 1981.

Balfour et al.; Pharmacology of nicotine and its therapeutic use in smoking cessation and neurodegenerative disorders; Pharmacology and Therapeutics; 72(1); pp. 51-81; Jan. 1, 1996.

Benowitz et al.; Sources of variability in nicotine and cotinine levels with use of nicotine nasal spray, transdermal nicotine, and cigarette smoking; British Journal of Clinical Pharmacology; 43(3); pp. 259-267; Mar. 1, 1997.

Benowitz et al.; Stable isotope studies of nicotine kinetics and bioavailability; Clin Pharm and Ther; 49(3); pp. 270-277; Mar. 1991.

Bordia et al.; Continuous and intermittent nicotine treatment reduces L-3 4-dihydroxyphenyalanine (L-DOPA)-induced dyskinesias in rat model of Parkinson's diseases; Journal of Pharmacology ans Experimental Therapeutics; 327(1); pp. 239-247; Oct. 1, 2008.

Bordia et al.; Partial recovery of striatal nicotinic receptors in 1-methyt-4-phenyl-1,2,3,6-tetrahydropyridine (MPTP)-lesioned monkeys with chronic oral nicotinic; The Journal of Pharmacology and Experimental Therapeutics; 319 (1); pp. 285-292; Oct. 1, 2006.

Bove et al.; Toxin-induced models of Parkinson's disease; NeuroRx; 2(3); pp. 484-494; Jul. 31, 2005.

Bricker et al.; Randomized controlled pilot trial of a smartphone app for smoking cessation using acceptance and commitment therapy; Drug and Alcohol Dependence; 143: pp. 87-94; Oct. 1, 2014 (Author Manuscript).

Brotchie et al.; Levodopa-induced dyskinesia in Parkinson's disease; Journal of Neural Transmission; 112(3); pp. 359-391; Mar. 1, 2005.

Bruguerolle; Chronopharmacokinetics; Clin Pharmacokinet; 35(2); pp. 83-94; Aug. 1998.

Calabresi et al.; Levodopa-induced dyskinesias inpatients with parkinson's disease: filling the bench-to-bedside gap; The Lancet Neurology; 9(11); pp. 1106-1117; Nov. 1, 2010.

Carta et al.; Role of striatal L-DOPA in the production of dyskinesia in 6-hydroxydopamine lesioned rats; Journal of Neurochemistry; 96(6); pp. 1718-1727; Mar. 2006.

Chen et al.; Enhanced striatal opioid receptor-mediated G-protein activation in L-DOPA-treated dyskinetic monkeys; Neuroscience; 132(2); pp. 409-420; Dec. 31, 2005.

Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.

Davie; A review of Parkinson's disease. British Medical Bulletin 2008 86(1): 109-127; Apr. 8, 2008.

De La Fuente et al.; The placebo effect in Parkinson's disease; Trends in Neuroscience; 25(6); pp. 302-306; Jun. 1, 2002.

Di Monte et al.; Relationship among nigrostriatal denervation, parkinsonism, and dyskinesias in the MPTP primate model; Movement Disorders; 15(3); pp. 459-466; May 1, 2000.

Dockser-Marcus, A.; New research shows drugs work best at certain times; The Wall Street Journal; 6 pgs,; May 27, 2003; (http://www.wsj.com/articles/SB105397312486508700).

Domino et al.; Nicotine alone and in combination with L-DOPA methyl ester or the D(2) agonist N-0923 in MPTP-induced chronic hemiparkinsonian monkeys; Exp Neurol; 1 58(2); pp. 414-421; Aug. 1999.

Dutil; Benzoyl Peroxide: Enhancing antibiotic efficacy in acne management; Skin Therapy Letter; 15(1); pp. 5-7; Nov./Dec. 2010.

Ebersbach et al.; Worsening of motor performance in patients with Parkinson's disease following transdermal nicotine administration; Movement Disorders; 14(6); pp. 1011-1013; Nov. 1, 1999.

Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.

Fagerstrom et al.; Nicotine may relieve symptoms of Parkinson's disease; Psychopharmacology; 116(1); pp. 117-119; Sep. 16, 1994.

Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.

Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.

Gennaro (Editor); Remington: The Science and Practice of Pharmacy; 19th Ed.; Mack Publishing Co.; Easton, PA; p. 1582-1584; Jun. 1995.

Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.

Gora; Nicotine transdermal systems; The Annals of Pharmacotherapy; 27(6); pp. 742-750; Jun. 1993.

Gotti et al.; Brain nicotinic acetylcholine receptors: native subtypes and their relevance; Treands in Pharmacological Sciences; 27(9); pp. 482-491; Sep. 30, 2006.

(56) References Cited

OTHER PUBLICATIONS

Green et al.; An oral formulation of nicotine for release and absorption in the colon: its development and pharmacokinetics. British Journal of Clinical Pharmacology; 48(4); pp. 485-493; Oct. 1999.
Gries et al.; Importance of Chronopharmacokinetics in Design and Evaluation of Transdermal Drug Delivery Systems; J Pharmoacol Exp Ther; 285(2); pp. 457-463; May 1998.
Guy; Current status and future prospects of transdermal drug delivery; Pharm Res; 13(12); pp. 1765-1769; Dec. 1996.
Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.
He et al.; Autoradiographic analysis of dopamine receptor-stimulated [35S]GTPtS binding in rat striatum; Brain Research; 885(1); pp. 133-136; Dec. 1, 2000.
He et al; Autoradiographic analysis of N-methyl-D-aspartate receptor binding in monkey brain: Effects of I-methyl-4-phenyl-I,2,3,6-tetrahydropyridine andlevodopa treatment; Neuroscience; 99(4); pp. 697-704; Aug. 23, 2000.
Heffner et al.; Feature-level analysis of a novel smartphone applicationn for smoking cessation; Am. J. Drug Alcohol Abuse; 41 (1); pp. 68-73; Jan. 2015 (Author Manuscript).
Hrushesky; Temporally optimizable delivery systems: sine qua non for the next therapeutic revolution; J Cont Rel; 19(1-3); pp. 363-368; Mar. 1992.
Hsu et al.; Effect of the D3 dopamine receptor partial agonist BP897 [N-[4-(4-(2-methoxyphenyl)piperazinyl) butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.
Huang et al.; Inhibitory effects of curcumin on in vitro lipoxygenase and cyclooxygenase activities in mouse epidermis; Cancer Res; 51(3); pp. 813-819; Feb. 1991.
Hukkanen et al.; Metabolism and disposition kinetics of nicotine; Pharmacological Reviews; 57(1); pp. 79-115; Mar. 1, 2005.
Hurley; Growing list of positive effects of nicotine seen in neurodegenerative disorders; Neurology Today; 12(2); pp. 37-38; Jan. 19, 2012.
Ingram el al.; Preliminary observations of oral nicotine therapy for inflammatory bowel disease: an open-label phase I-II study of tolerance; Inflamm Bowel Diseases; 11(12); pp. 1092-1096; Dec. 1, 2005.
Janson et al.; Chronic nicotine treatment counteracts dopamine D2 receptor upregulation induced by a partial meso-diencephalic hemitransection in the rat; Brain Res.; 655(1-2); pp. 25-32; Aug. 29, 1994.
Jarvik et al.; Inhibition of cigarette smoking by orally administered nicotine; Clinical Pharmacology and Therapeutics; 11(4); pp. 574-576; Jul. 1, 1970.
Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.
Jeyarasasingam et al.; Stimulation of non-o7 nicotinic receptors partially protects dopaminergic neurons from I-methyl-4-phenylpyridinium-induced toxicity in culture; Neuroscience; 109(2); pp. 275-285; Jan. 28, 2002.
Jeyarasasingam et al.; Tacrine, a reversible acetylcholinesterase inhibitor, induces myopathy; Neuroreport; 11 (6); pp. 1173-1176; Apr. 27, 2000.
Kalish et al.; Prevention of contact hypersensitivity to topically applied drugs by ethacrynic acid: potential application to transdermal drug delivery; J. Controll Rel; 48(1); pp. 79-87; Sep. 1997.
Kalish et al.; Sensitization of mice to topically applied drugs: albuterol, chlorpheniramine, clonidine and nadolol; Contact Dermatitis; 35(2); pp. 76-82; Aug. 1996.
Kelton et al.; The effects of nicotine on Parkinson's disease; Brain Cognition; 43(1-3); pp. 274-282; Jun. 2000.

Kennelly; Microcontrollers drive home drug delivery; 3 pgs; posted Jul. 2014; (retrieved Jul. 26, 2016 from the internet: http://electronicsmaker.com/microcontrollers-drive-home-drug-delivery-2.
Kiwi Drug; Buy nicorette microtabs; 3 pages; retrieved from the internet (www.kiwidrug.com/search/nicorette_microtabs); on Jul. 26, 2018.
Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.
Kulak et al.; 5-Iodo-A-85380 binds to oconotoxin Mil-sensitive nicotinic acetylcholine receptors (nAChRs) as well as o4j32* subtypes; Journal of Neurochemistry; 81(2); pp. 403-406; Apr. 1, 2002.
Kulak et al.; Declines in different pi* nicotinic receptor populations in monkey striatum after nigrostriatal damage; The Journal of Pharmacology and Experimental Therapeutics; 303(2); pp. 633-639; Nov. 1, 2002.
Kulak et al.; Loss of nicotinic receptors in monkey striatum after I-mefhyl-4-phenyl-1,2,3,6-tetrahydropyridine treatment is due to a decline in oconotoxin Mil sites; Molecular Pharmacology; 61(1); pp. 230-238; Jan. 1, 2002.
Kumar et al.; Levodopa-dyskinesia incidence by age of Parkinson's disease onset; Movement disorders; 20(3); pp. 342-344; Mar. 2005.
Kydonieus et al. (Editors); Biochemical Modulation of Skin Reactions; CRC Press; Boca Ratan, FL; pp. 9-10; Dec. 1999.
Labrecque, G. et al.; Chronopharmacokinetics; Pharmaceutical News; 4(2); pp. 17-21; (year of pub. sufficiently earlier than effective US filing date and any foreign priority date) 1997.
Lai et al.; Long-term nicotine treatment decreases striatal a6* nicotinic acetylcholine receptor sites and function in mice; Molecular Pharmacology; 67(5); pp. 1639-1647; May 1, 2005.
Lai et al.; Selective recovery of striatal 1251-a-conotoxinMII nicotinic receptors after nigrostriatal damage in monkeys; Neuroscience; 127(2); pp. 399-408; Dec. 31, 2004.
Lamberg; Chronotherapeutics: Implications for drug therapy; American Pharmacy; NS31(11); pp. 20-23; Nov. 1991.
Langston et al.; Investigating levodopa-induced dyskinesias in the parkinsonian primate; Annals of Neurology; 47(4 Suppl 1); pp. S79-S88; Apr. 2000.
Laser et al.; A review of micropumps; J. of Micromech. and Microeng.; 14; pp. R35-R64; Apr. 2004.
Lee et al.; A comprehensive review of opioid-induced hyperalgesia; Pain Physician; 14; pp. 145-161; Mar. 2011.
Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.
Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.
Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.
Lemmer; The clinical relevance of chronopharmacology in therapeutics; Pharmacological Research; 33(2); pp. 107-115; Feb. 1996.
LeWitt et al.; New developments in levodopa therapy; Neurology; 62(No. 1, Suppl. 1); pp. S9-S16; Jan. 2004.
Lieber Man; Compressed tablets by direct compression; Pharmaceutical Dosage forms; vol. 1, 2nd ed.; Marcel Dekker Inc.; pp. 195-246; (year of pub. sufficiently earlier than effective US filing date and any foreign priority date) 1989.
Lieberman; Compression—coated and layer tablets; Pharmaceutical Dosage forms; vol. 1, 2nd ed.; Marcel Dekker Inc.; pp. 266-271; (year of pub. sufficiently earlier than effective US filing date and any foreign priority date) 1989.
Lundblad et al.; Cellular and behavioural effects of the adenosine A2a receptor antagonist KW-6002 in a rat model of I-DOPA-induces Dyskinesia; Journal of Neurochemistry; 84(6); pp. 1398-1410; Mar. 2003.

(56) References Cited

OTHER PUBLICATIONS

Madandla et al,; Voluntary running provides neuroprotection in rats after6-hydroxydopamine injection into the medial forebrain bundle; Metabolic Brain Disease; 19(1-2); pp. 43-50; Jun. 2004.
Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.
Matta et al.; Guidelines on nicotine dose selection for in vivo research; Psychopharmacology (Berl.); 190(3); pp. 269-319; Feb. 1, 2007.
McCallum et al,; Decrease in alpha3*/alpha6* nicotinic receptors in monkey brain after nigrostriatal damage; Molecular Pharmacology; 68(3); pp. 737-746; Sep. 2005.
McCallum et al.; Compensation in pre-synaptic dopaminergic function following nigrostriatal damage in primates; Journal of Neurochemistry; 96(4); pp. 960-972; Feb. 1, 2006.
McCallum et al.; Differential regulation of mesolimbic alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.
McCallum el al.; Increases in aplha 4* but not aplha3*/alpha6* nicotinic receptor sites and function in the primate striatum following chronic oral nicotine treatment; Journal of Neurochemistry; 96(4); pp. 1028-1041; Feb. 2006.
McNeil Sweden AB. Package Leaflet: Information for the user. Nicorette Microtab Lemon 2mg sublingual tablets. (This leaflet was last approved in Apr. 16, 2008). retrived from ( www.lakemedelsverket.se/SPC _PIL/Pdf/enhumpil/Nicorette%20Microtab%20Lemon%202mg%20sublingual%20tablet%20ENG.pdf.) Accessed Aug. 19, 2010.
Medtronic; MiniMed Paradigm® Veo(TM) System (product info.); retrieved May 12, 2015from the internet: (http://www.medtronic.co.uk/your-health/diabetes/device/insulin-pumps/paradigm-veo-pump/); 3 pgs.
Meissner et al.; Priorities in parkinson's disease research; Nature reviews Drug Discovery; 10(5); pp. 377-393; May 1, 2011.
Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.
Merck manual of therapy and diagnosis; 17th edition. Merck Research Laboratories; pp. 1466-1471; (year of pub. sufficiently earlier than effective US filing date and any foreign priority date) 1999.
Meredith et al.; Behavioral models of Parkinson's disease in rodents: a new look at an old problem; Movement Disorders; 21(10); pp. 1595-1606; Oct. 1, 2006.
Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; (year of pub. sufficiently earlier than effective US filing date and any foreign priority date) 2002.
Meshul et ai.; Nicotine alters striatal glutamate function and decreases the apomorphine-induced contralateral rotations in 6-OHDA-lesioned rats; Experimental Neurology; 175(1); pp. 257-274; May 31, 2002.
Molander et al.; Reduction of tobacco withdrawal symptoms with a sublingual nicotine tablet: A placebo controlled study; Nictonie & Tob. Res.; 2(2); pp. 187-191; May 2000.
Murphy et al.; Transdermal drug delivery systems and skin sensitivity reactions. Incidence and management; Am. J. Clin Dermatol.; 1(6); pp. 361-368; Nov./Dec. 2000.
Mutalik et al.; Glibenclamide transdermal patches: physicochemical, pharmacodynamic, and pharmacokinetic evaluation; J Pharm Sci; 93(6); pp. 1577-1594; Jun. 2004.
Mutalik et al.; Glipizide matrix transdermal systems for diabetes mellitus: preparation, in vitro and preclinical studies; Life Sci; 79(16); pp. 1568-1567; Sep. 2006.

Nakadate et al.; Effects of chalcone derivatives on lipoxygenase and cyclooxygenase activities of mouse epidermis; Prostaglandins; 30(3); pp. 357-368; Sep. 1985.
National Institute of Neurological Disorders and Stroke. Parkinson's Disease: Hope Through Research. 54 pages; Retrieved from the internet (https://catalog.ninds.nih.gov/pubsfatic//15-139/15-139.pdf) on Jan. 15, 2018.
Newhouse et al.; Nicotine treatment of mild cognitive impairment: a 6-month double-blind pilot clinical trial; Neurology; 78(2); pp. 91-101; Jan. 10, 2012.
Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.
Ohdo; Changes in toxicity and effectiveness with timing of drug administration: implications for drug safety; Drug Safety; 26(14); pp. 999-1010; Dec. 2003.
Olanow; The scientific basis for the current treatment of Parkinson's disease; Annu. Rev. Med.; 55; pp. 41-60; Feb. 18, 2004.
Olsson et al.; A valve-less planar pump in silicon; IEEE; The 8th International Conference on Solid-State Sensors and Actuators; vol. 2; pp. 291-294, Jun. 1995.
Olsson et al.; An improved valve-less pump fabricated using deep reactive ion etching; Proc. of the IEEE, 9th Int'l Workshop on MEMS: San Diego, CA; pp. 479-484; Feb. 11-15, 1996.
O'Neill et al.; The role of neuronal nicotinic acetylcholine receptors in acute and chronic neurodegeneration; Current Drug Targets-CNS and Neurological Disorders; 1(4); pp. 399-412; Aug. 1, 2002.
Parkinson Study Group; Levodopa and the progression of Parkinson's disease; N Engl J Med.; 351; pp. 2498-2508; Dec. 9, 2004.
Petzinger et al.; Reliability and validity of a new global dyskinesia rating scale in the MPTP-lesioned non-human primate; Movement Disorders; 16(2); pp. 202-207; Mar. 1, 2001.
Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.
Prosise et al.; Effect of abstinence from smoking on sleep and daytime sleepiness; Chest; 105(4); pp. 1136-1141; Apr. 1994.
Quik et al.; Chronic oral nicotine normalizes dopaminergic function and synaptic plasticity in I-methyl-4-phenyl-I,2,3,6-tetrahydropyridine-lesioned primates; The Journal of Neuroscience; 26(17); pp. 4681-4689; Apr. 26, 2006.
Quik et al.; Chronic oral nicotine treatment protects against striatal degeneration in MPTP-treated primates; Journal of Neurochemistry; 98(6); pp. 1866-1875; Sep. 1, 2006.
Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.
Quik et al.; Differential declines in striatal nicotinic receptor subtype function after nigrostriatal damage in mice; Molecular Pharmacology; 63(5); pp. 1169-1179; May 1, 2003.
Quik et al.; Differential nicotinic receptor expression in monkey basal ganglia: Effects of nigrostriatal damage; Neuroscience; 112(3); pp. 619-630; Jul. 5, 2002.
Quik et al.; Expression of D3 receptor messenger RNA and binding sites in monkey striatum and substantia nigra after nigrostriatal degeneration: Effect of levodopa treatment.;Neuroscience; 98(2); pp. 263-273; Jun. 30, 2000.
Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.
Quik et al.; L-DOPA treatment modulates nicotinic receptors in monkey striatum; Mol Pharmacol; 64(3); pp. 619-628; Sep. 2003.
Quik et al.; Localization of nicotinic receptor subunit mRNAs in monkey brain by in situ hybridization; The Journal of Comparative Neurology; 425(1); pp. 58-69; Sep. 11, 2000.
Quik et al.; Loss of a-conotoxinMII- and A85380-sensitive nicotinic receptors in Parkinson's disease striatum; Journal of Neurochemistry; 88(3); pp. 668-679; Feb. 1, 2004.
Quik et al.; Nicotine administration reduces striatal MPP+ levels in mice; Brain Research; 917(2); pp. 219-224; Nov. 2, 2001.

(56) References Cited

OTHER PUBLICATIONS

Quik et al.; Nicotine and nicotinic receptors; relevance to Parkinson's disease; Neurotoxicology; 23(4-5); pp. 581-594; Oct. 2002.
Quik et al.; Nicotine and Parkinson's disease: implications for therapy; Movement Disorders; 23(12); pp. 1641-1652; (Author Manuscript); Sep. 1, 2008.
Quik et al.; Nicotine as a potential neuroprotective agent for Parkinson's disease; Movement disorders; 27(8); pp. 947-957; Jul. 1, 2012.
Quik et al.; Nicotine neuroprotection against nigrostriatal damage: importance of the animal model; Trends in Pharmacological sciences; 28(5); pp. 229-235; May 31, 2007.
Quik et al.; Nicotine reduces levodopa-induced dyskinesias in lesioned monkeys; Annals of neurology; 62(6); pp. 588-596; (Author Manuscript); Dec. 1, 2007.
Quik et al.; Nicotinic receptors and Parkinson's disease; European Journal of Pharmacology; 393(1); pp. 223-230; Mar. 30, 2000.
Quik et al.; Striatal a6* nicotinic acetylcholine receptors: Potential targets for Parkinson's disease therapy; The Journal of Pharmacology and Experimental Therapeutics; 316(2); pp. 481-489; Feb. 1, 2006.
Quik et al.; Subunit composition of nicotinic receptors in monkey striatum: Effect of treatments with I-methyl-4-phenyl-I,2,3,6-tetrahydropyridine or L-DOPA; Molecular Pharmacology; 67(1): pp. 32-41; Jan. 2005.
Quik et al.; Vulnerability of 125I-a-conotoxin Mil binding sites to nigrostriatal damage in monkey; The Journal of Neuroscience; 21(15); pp. 5494-5500; Aug. 1, 2001.
Quik; Smoking, nicotine and Parkinson's disease; Trends in Neurosciences; 27 (9); pp. 561-568; Sep. 2004.
Redfern et al.; Circadian rhythms, jet lag, and chronobiotics: An overview; Chronobiology International; 11(4); pp. 253-265; Aug. 1994.
Reinberg; Concepts of Circadian Chronopharmacology; Annals of the New York Academy of Sciences; 618 (Temporal Control of Drug Delivery); pp. 102-115; Feb. 1991.
Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.
Samii et al.; Parkinson's disease; The Lancet; 363(9423); pp. 1783-1793; May 29, 2004.
Savitt et al.; Diagnosis and treatment of Parkinson disease: molecules to medicine; The Journal of Clinical Investigation; 116(7); pp. 1744-1754; Jul. 3, 2006.
Schapira; Disease modification in Parkinson's disease; The Lancet Neurology; 3(6); pp. 362-368; Jun. 30, 2004.
Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.
Schneider et al.; Effects of the nicotinic acetylcholine receptor agonist SIB-1508Y on object retrieval performance in MPTP-treated monkeys: Comparison with levodopa treatment; Annals of Neurology; 43(3); pp. 311-317; Mar. 1, 1998.
Schober et al.; Classic toxin-induced animal models of Parkinson's disease: 6-OHDA and MPTP; Cell and Tissue Research; 318(1); pp. 215-224; Oct. 1, 2004.
Shin et al.; Enhanced bioavailability of triprolidine from the transdermal TPX matrix system in rabbits; Int. J. Pharm.; 234(1-2); pp. 67-73; Mar. 2002.
Silver et al.; Transdermal nicotine and haloperidol in Tourette's disorder: a double-blind placebo-controlled study; Journal of Clinical Psychiatry; 62(9); pp. 707-714; Sep. 1, 2001.
Singer et al.; Nightmares in patients with Alzheimer's disease caused by donepezii: Therapeutic effect depends on the time of intake; Nervenarzt; 76(9); pp. 1127-1129; Sep. 2005 (Article in German w/ Eng. Summary).
Star Micronics Co., LTD; Prototype Diaphragm Micro Pump SDMP305 (specifications); retrieved May 12, 2015 from the internet archive as of Jul. 2006 (http://www.star-m.jp/eng/products/develop/de07.htm); 3 pgs.
Stocchi et al.; Motor fluctuations in levodopa treatment: clinical pharmacology; European Neurology; 36(Suppl 1); pp. 38-42; Jan. 1996.
Strong et al.; Genotype and smoking history affect risk of levodopa-induced dyskinesias in parkinson's disease; Movement Disorders; 21(5); pp. 654-659; May 1, 2006.
Thiele et al. (Ed.); Oxidants and Antioxidants in Cutaneous Biology: Current Problems in Dermatology (Book 29); S. Karger; 196 pgs.; Feb. 2001.
Togasaki et al.; Dyskinesias in normal squirrel monkeys induced by nomifensine and levodopa; Neuropharmacology; 48(3); pp. 398-405; Mar. 31, 2005.
Togasaki et al.; Levodopa induces dyskinesias in normal squirrel monkeys; Annals of Neurology; 50(2); pp. 254-257; Aug. 1, 2001.
Togasaki et al.; The Webcam system: A simple, automated, computer-based video system for quantitative measurement of movement of nonhuman primates; Journal of Neuroscience Methods; 145(1); pp. 159-166; Jun. 30, 2005.
Tolosa et al.; Antagonism by piperidine of levodopa effects in Parkinson disease; Neurology; 27(9); pp. 875-877; Sep. 1, 1977.
U.S. Department of Health and Human Services, Food and Drug Administration, Center for Drug Evaluation and Research (CDER); Guidance for industry: Abuse-deterrent opioids-Evaluation and labeling; 24 pages; retrieved from the internet (http//www.fda.gov/downloads/drugs/guidancecomplainceregulatoryinformation/guidances/ucm344743.pdf); Jan. 2013.
United States of America VA/DoD; Tapering and discontinuing opioids; 2 pages; retrieved from the internet (http://www.healthquality.va.gov/guidelines/Pain/cot/OpioidTaperingFactSheet23May2013v1.pdf); on Sep. 1, 2016.
Vieregge et al.; Transdermal nicotine in PD: A randomized, double-blind, placebo-controlled study; Neurology; 57(6); pp. 1032-1035; Sep. 25, 2001.
Villafane et al.; Long-term nicotine administration can improve Parkinson's disease: report of a case after three years of treatment; Revista Neurologica Argentina; 27(2); pp. 95-97; (year of pub. sufficiently earlier than effective US filing date and any foreign priority date) 2002.
Warburton et al.; Facilitation of learning and state dependency with nicotine; Psychoparmacology; 89(1); pp. 55-59; May 1, 1986.
Wermuth et al.; Glossary of terms used in medicinal chemistry Pure & Appl. Chem., vol. 70(5); 1129-1143; 1998 AC recommendations 1998); Pure and Applied Chemistry; 70(5); pp. 1129-1143; Jan. 1998.
Wesnes et al.; Effects of scopolamine and nicotine on human rapid information processing performance; Psychoparmacology; 82(3); pp. 147-150; Sep. 1, 1984.
Westman et al.; Oral nicotine solution for smoking cessation: a pilot tolerability study; Nicotine and Tobacco Research; 3(4); pp. 391-396; Nov. 1, 2001.
Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.
Wille et al.; Inhibition of irritation and contact hypersensitivity by ethacrynic acid; Skin Pharm Appl Skin Physiol; 11(4-5); pp. 279-288; Jul. 1998.
Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.
Wille et al.; Several different ion channel modulators abrogate contact hypersensitivity in mice; Skin Pharm Appl Skin Physiol; 12(1-2); pp. 12-17; Jan. 1999.
Wille, J.; Novel topical delivery system for plant derived hydrophobic anti-irritant active (presentation abstract No. 273); 226th ACS National Meeting; New York, NY; Sep. 7-11, 2003.
Wille; In Closing: an editorial on Plant-Derived Anti-irritants. Cosmetics & Toiletries, 118 (8), Aug. 2003.

(56) References Cited

OTHER PUBLICATIONS

Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.
Wille; Thixogel: Novel topical delivery system for hydrophobic plant actives; in ROSEN (Ed.) Delivery System Handbook for Personal Care and Cosmetic Products; 1st Ed.; ISBN: 978-0-8155-1504-3; pp. 762-794; Sep. 2005.
Youan; Chronopharmaceutics: gimmick or clinically relevant approach to drug delivery?; J Cont Rel; 98(3); pp. 337-353; Aug. 2004.
Yun et al.; A distributed memory MIMD multi-computer with reconfigurable custom computing capabilities; IEEE; Proc. Int'l. Conf. on Parallel and Distributed Systems; pp. 8-13; Dec. 10-13, 1997.
Zubieta et al.; Placebo effects mediated by endogenous opioid activity on mu-opioid receptors; 25(34); pp. 7754-7762; Aug. 24, 2005.
Dipierro; U.S. Appl. No. 16/799,578 entitled "Biosynchronous transdermal drug delivery," filed Feb. 24, 2020.
Arora et al.; U.S. Appl. No. 16/474,083 entitled "Methods and devices for treating levodopa induced dyskinesia," filed Jan. 15, 2020.
Zumbrunn et al.; U.S. Appl. No. 16/933,836 entitled "Transdermal drug delivery method and system," filed Jul. 20, 2020.
Ruane et al.; U.S. Appl. No. 17/293,570 entitled "Thermally regulated transdermal drug delivery system," filed May 13, 2021.

\* cited by examiner

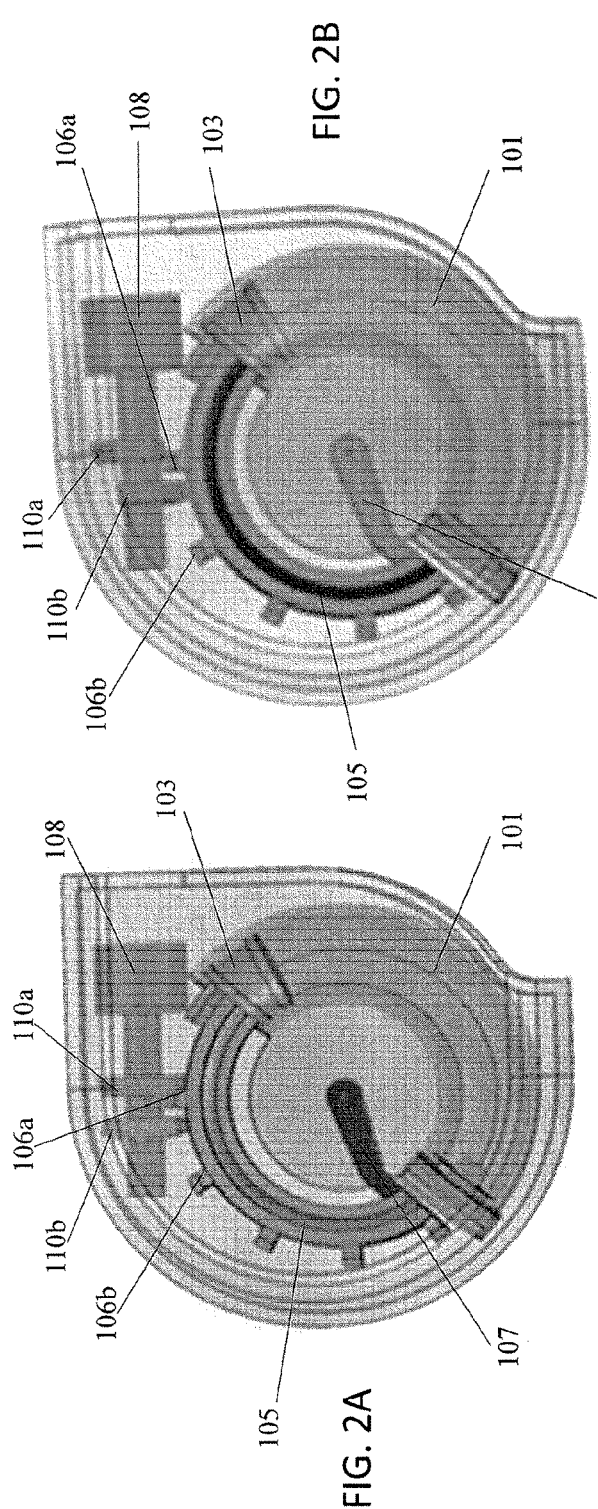
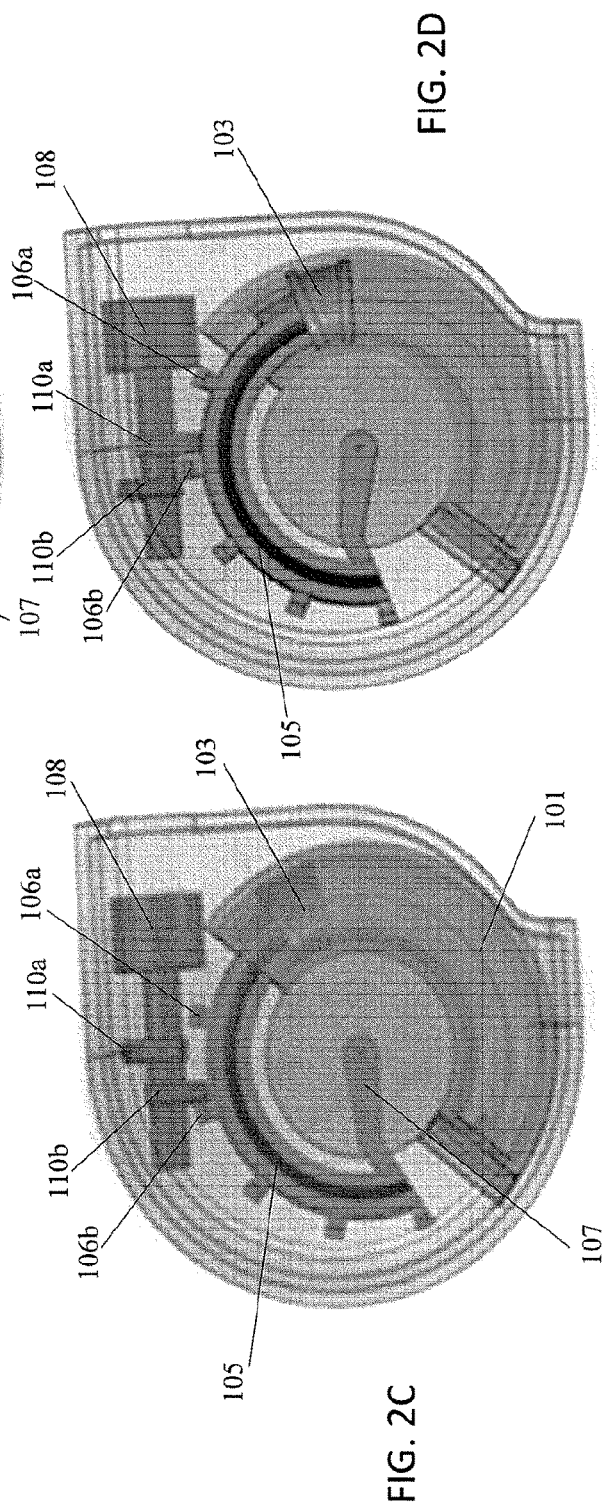

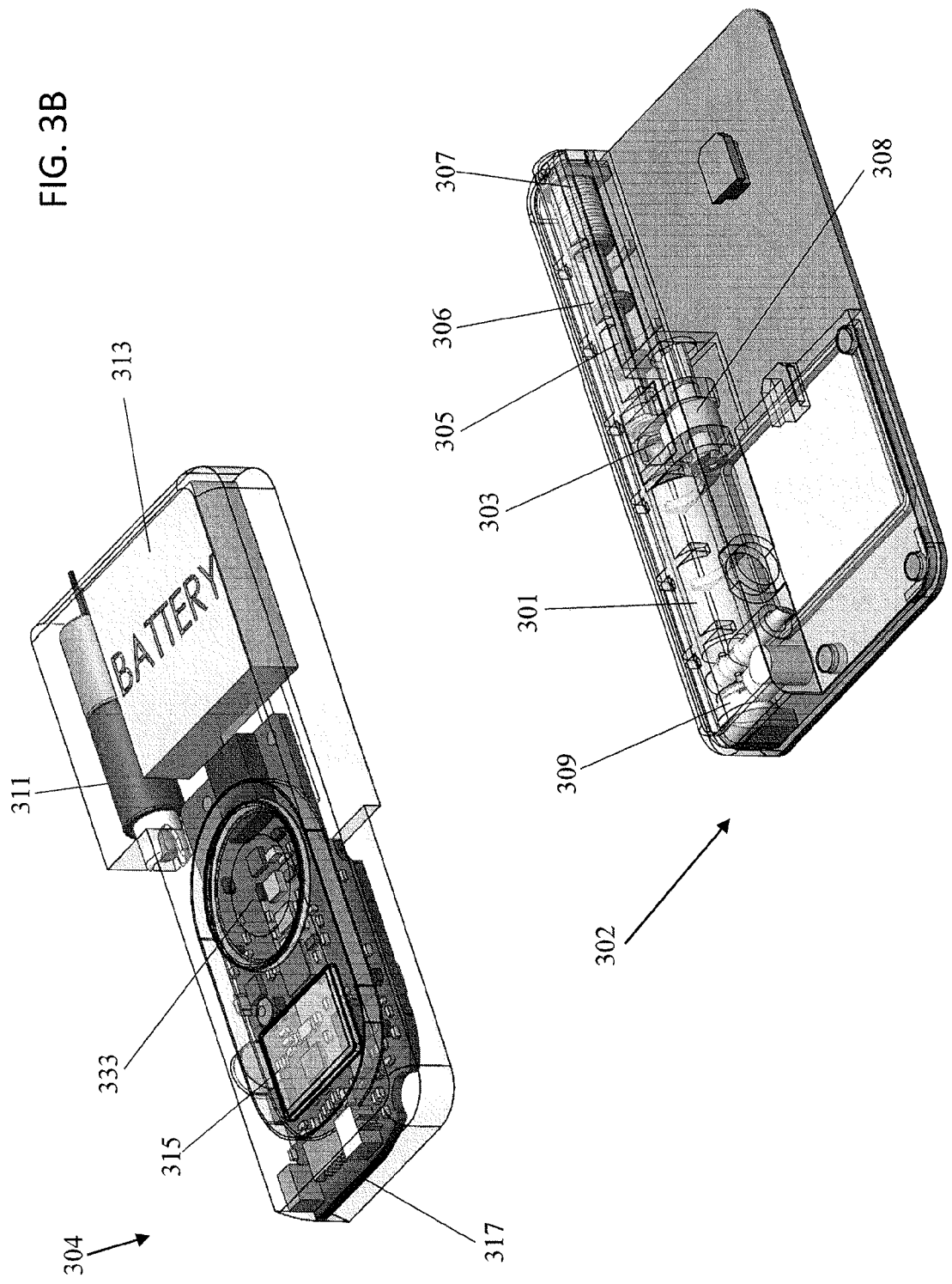

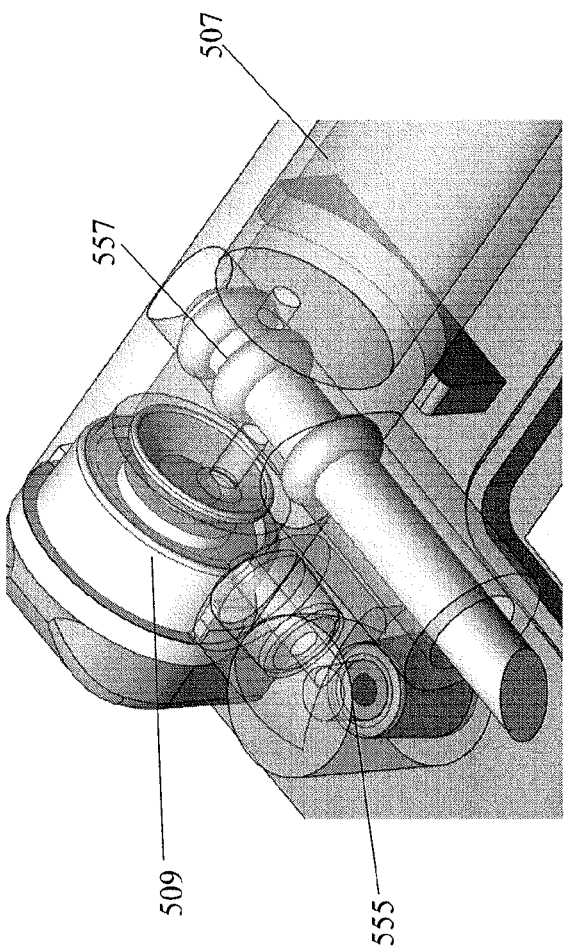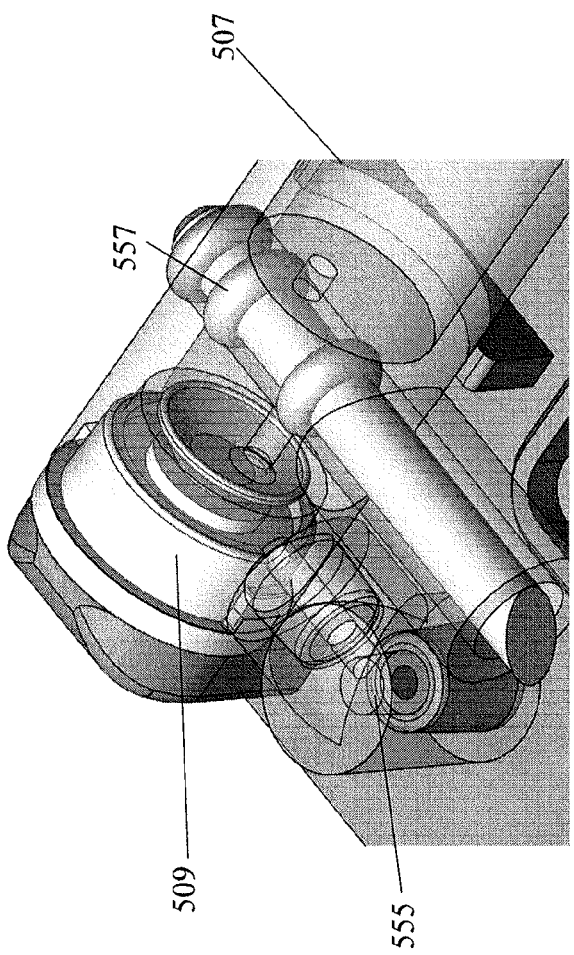
FIG. 5A
FIG. 5B

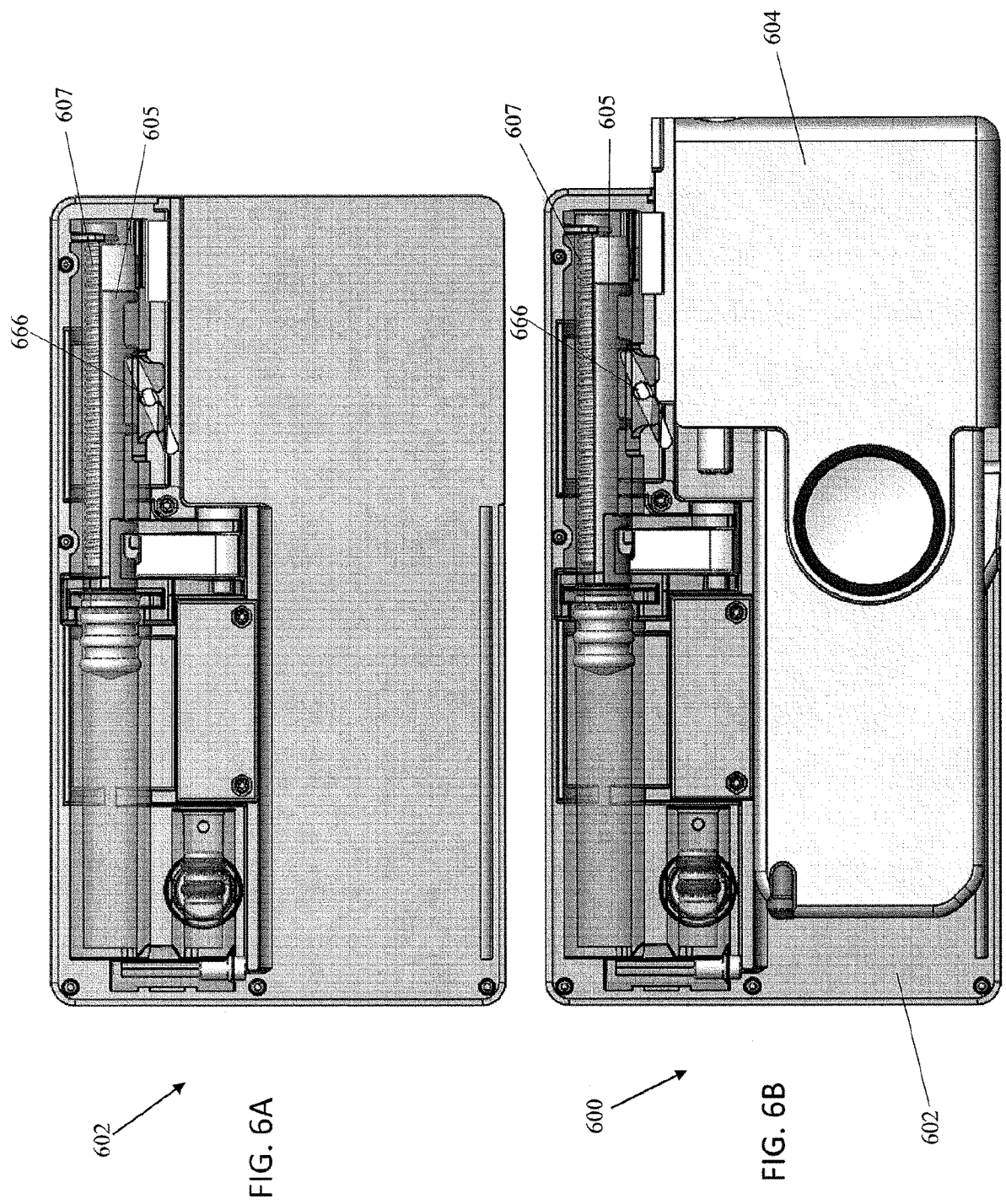

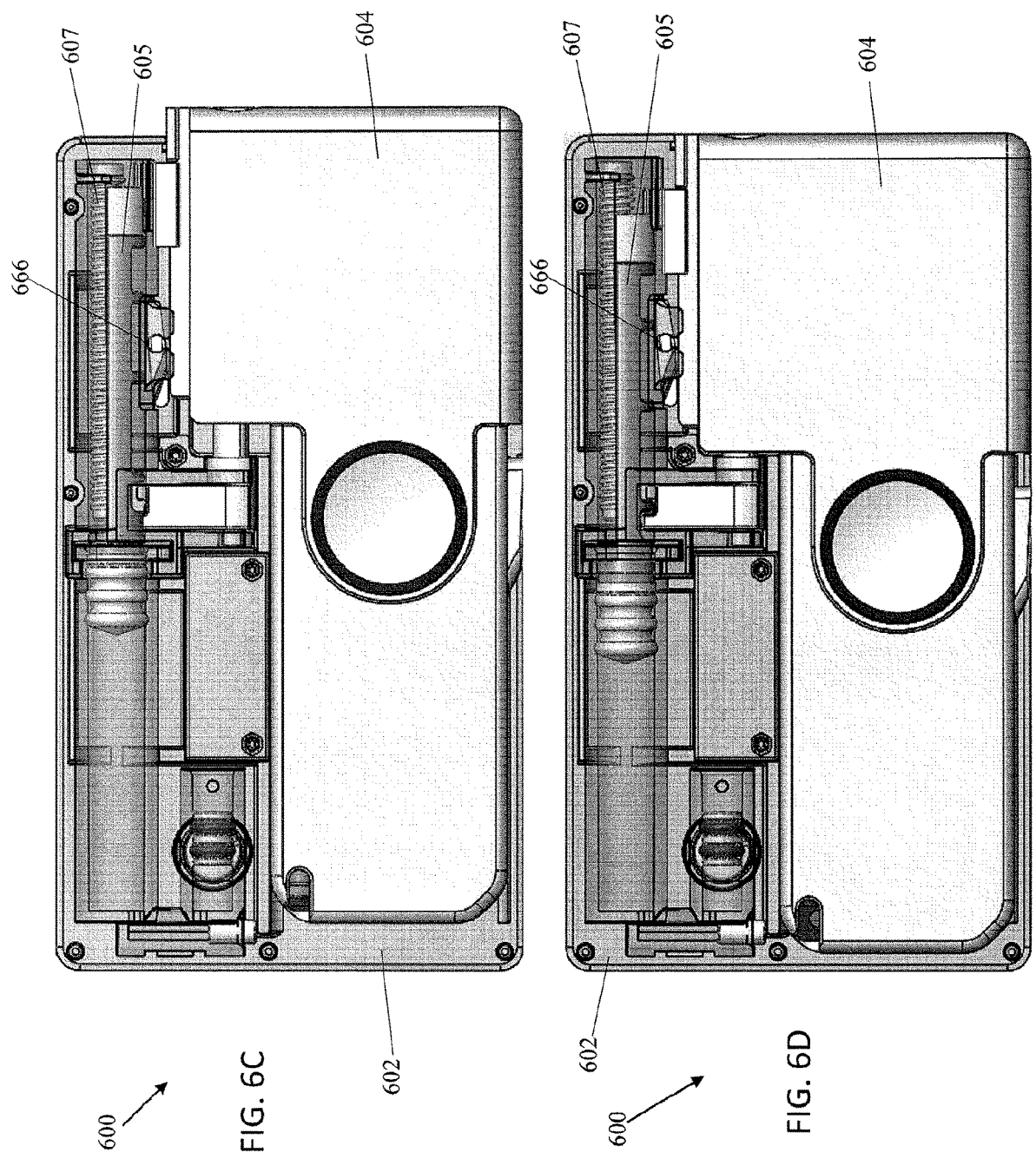

TRANSDERMAL DRUG DELIVERY DEVICES AND METHODS

CROSS REFERENCE TO RELATED APPLICATIONS

This application claims priority to U.S. Provisional Application No. 62/443,421, filed Jan. 6, 2017, and titled "TRANSDERMAL DRUG DELIVERY DEVICES AND METHODS", the entirety of which is incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates generally to devices and methods for providing a formulation to a patient transdermally.

BACKGROUND

Medicinal drugs are given to people to manage or improve their health for a variety of reasons, such as to manage nicotine or another addiction or dependency, to manage pain, or to prevent or treat a medical condition or disease such as diabetes, Parkinson's disease, or ulcerative colitis.

Some medicinal drugs are rapidly metabolized by the body. Multiple doses of the drug over a period of time are therefore often needed to provide a desired effect. In addition to having the desired preventative or therapeutic effects, medicinal drugs can also have negative side-effects on the body that can range from irritating to life-threatening. A person's body can also develop tolerance to a drug and experience a diminished response to the drug after taking it for a period of time and require higher doses to have an effect, resulting in increased drug use and additional side-effects. It is therefore beneficial to a person taking a drug to dose the drug properly to reduce tolerance and/or side-effects.

Transdermal drug delivery is one way to deliver medicinal drugs to a patient. However, current transdermal drug delivery systems can be improved by any one of: a size reduction, a smaller volume, a lower profile to reduce the height and/or cross-sectional foot print, a reduced weight, reduction of moving parts, a reduction of expensive parts, a decreased cost, a reduced engagement force between the reusable part and drug cartridge, and more accurate dosage delivery.

Accordingly, a transdermal drug delivery system that provides some or all of these improvements is desired.

SUMMARY OF THE DISCLOSURE

The present invention relates generally to systems for delivering a formulation transdermally and methods for using the systems to deliver the formulation.

In general, in one embodiment, a transdermal drug delivery device includes a reservoir, a transdermal membrane, a piston, a control rod, a spring, and a rotational cam. The reservoir is configured to hold a formulation therein. The transdermal membrane is configured to allow the formulation from the reservoir to pass therethrough. The piston is configured to move into the reservoir. The control rod is attached to the piston and includes a plurality of teeth thereon. The spring is configured to apply force to the control rod in the direction of the reservoir. The rotational cam has a first camming surface and a second camming surface that are configured to engage with the plurality of teeth. The rotational cam, when rotated, is configured to disengage the first camming surface from a first tooth of the plurality of teeth, thereby allowing the spring to advance the piston into the reservoir to expel the formulation onto the transdermal membrane.

This and other embodiments can include one or more of the following features. The transdermal drug delivery device can further include a motor configured to rotate the rotational cam. The device can include a first part that includes the reservoir, membrane, piston, control rod, spring, and rotational cam and a second part that includes the motor and a power source. The first and second parts can be configured to engage and disengage from one another. The first part can be disposable, and the second part can be reusable. The first part can further include a storage latch that is configured to hold the spring away from the control rod during storage. The storage latch can be configured to release the spring when the first and second parts are engaged. The transdermal drug delivery device can further include a user interface and a display. The control rod and plunger can have a substantially linear configuration. The reservoir can have a substantially linear shape. The control rod and plunger can have a curved configuration. The reservoir can have a semi-annular shape. A spacing between the plurality of teeth on the control rod can define a teeth spacing pattern, and the teeth spacing pattern can correspond to a drug delivery profile of the transdermal drug delivery device. The teeth spacing pattern can have a substantially uniform spacing. A distance between the first and second camming surfaces can be substantially equivalent to a distance between adjacent teeth. The teeth spacing pattern can have a non-uniform spacing. The drug delivery profile can correspond to a circadian rhythm or a bio-synchronous pattern of a patient using the transdermal drug delivery device. The first and second camming surfaces can be circumferentially offset from one another. The first and second camming surfaces may not overlap circumferentially. The device can be configured such that, after the first camming surface disengages from the first tooth and pushes the spring to push the control rod and piston into the reservoir, the second camming surface engages with a second tooth of the plurality of teeth to stop the piston from moving further into the reservoir. The cam can be rotatable in a first direction to cause the first camming surface to disengage with the first tooth and the second camming surface to engage with the second tooth. The cam can be rotatable in a second direction to cause the second camming surface to disengage from the second tooth and cause the piston to move further into the reservoir to expel more of the formulation. The cam can be rotatable alternately in the first and second directions to allow sequential bolus deliveries of the formulation. The cam can be rotatable a first distance in a first direction to cause the first camming surface to disengage with the first tooth and the second camming surface to engage with the second tooth. The cam can be rotatable a second distance in the first direction to cause the second camming surface to disengage from the second tooth and cause the piston to move further into the reservoir to expel more of the formulation. The spring can be configured to apply a force of about 12 N or less to move the control rod. The transdermal drug delivery can further include a pathway between the reservoir and the transdermal membrane. The transdermal drug delivery device can further include a valve along the pathway between the reservoir and the transdermal membrane. The formulation can be selected from the group consisting of: nicotine, Acamprosate, Acetaminophen, Alfentanil, Allopurinol, Almotriptan, Alprazolam, Amitriptylinem, Amoxapine, Apomorphine, Aripiprazole, Armodafinil, Asenapine, Atomoxetine, Azelastine, Baclofen, Benzbromarone, Benzydamine, Brexpiprazole, Budesonide, Bupivacaine, Buprenorphine, Buprenorphine, Bupropion, Buspirone, Cabergoline, Capsaicin, Carbamazepine, Carbidopa, Carisprodol, Celecoxib, Citalopram, Clobazam, Clonazepam, Clonidine, Clopidogrel, Colchicine, Cyclobenzaprine, Dalteparin, Desvenlafaxine, Dexamfetamine, Dexmethylphenidate, Diazepam, Diclofenac, Disulfiram, Divalproex, Dolasetron, Doxepin, Dronabinol, Droxidopa, Duloxetine, Eletriptan, Entacapone, Escitalopram, Eslicarbazepine, Esomeprazole, Estradiol, Estrogen, Eszopiclone, Ethosuximide, Etodolac, Ezogabine, Febuxostat, Felbamate, Fenbufen, Fentanyl, Flunisolide, Fluorouracil, Fluoxetine, Fluticasone, Fluvoxamine, Formoterol, Fosphenytoin, Frovatriptan, Gabapentin, Granisetron, Guanfacine, Hydrocodone, Hydrocodone, Hydrocortisone, Hydromorphone, Hydroxyzine, *Hypericum* Extract, Ibuprofen, Indometacin, Ketorolac, Lacosamide, Lamotrigine, Levetiracetam, Levodopa, Levomilnacipran, Levosalbutamol, Lidocaine, Lisdexamfetamine, Lithium, Lorazepam, Lorcaserin, Losartan, Loxapine, Meclizine, Meloxicam, Metaxalone, Methylphenidate, Milnacipran, Mirtazapine, Modafinil, Morphine, Nabilone, Nadolol, Naloxone, Naltrexone, Naproxen, Naratriptan, Nedocromil, Nefazodone, Nitroglycerin, Olanzapine, Ondansetron, Orlistat, Oxaprozin, Oxcarbazepine, Oxybutynin, Oxycodone, Oxymorphone, Palonosetro, Pamidronate, Paroxetine, Perampanel, Phentermine, Phentolamine, Pramipexole, Prasugrel, Prazepam, Prednisone, Pregabalin, Procaine, Promethazine, Propofol, Quetiapine, Ramelteon, Rasagiline, Remifentanil, Risperidone, Rivastigmine, Rizatriptan, Ropinirole, Ropivacaine, Rotigotine, Rufinamide, Salbutamol, Scopolamine, Selegiline, Sertraline, Sodium Oxybate, Strontium, Sufentanil, Sumatriptan, Suvorexant, Tapentadol, Tasimelteon, Temazepam, Testosterone, Tetracaine, Theophylline, Tiagabine, Tiotropium, Tirofiban, Tolcapone, Topiramate, Tramadol, Trazodone, Triazolam, Trimipramine, Valproic acid, Venlafaxine, Vigabatrin, Vilazodone, Vortioxetine, Zaleplon, Zileuton, Ziprasidone, Zolmitriptan, Zolpidem, Norethisterone, Enalapril, Ethinyl Estradiol, Insulin, Memantine, Methamphetamine, Norelgestromine, Pergolide, Ramipril, Tecrine, Timolol, Tolterodine, and Zonisamide. The transdermal membrane can include polypropylene. The transdermal drug delivery device can further include an adhesive for adhering the transdermal drug delivery device to a skin of a patient. A length of the transdermal drug delivery device can be between 60-80 mm, a width can be between 30-45 mm, and a thickness can be between 6-12 mm. A volume of the transdermal drug delivery device can be between 15 and 30 cm3.

In general, in one embodiment, a method of transdermal drug delivery includes: (1) applying a transdermal delivery system to the skin of a patient, the transdermal delivery system including a reservoir, a transdermal membrane, a piston, a control rod with a plurality of teeth, and a rotational cam having first and second camming surfaces; (2) rotating the cam such that the first camming surface moves from a first position that engages with a first tooth of the plurality of teeth to a second position that disengages with the first tooth such that the piston advances and pushes a first dose of a formulation out of the reservoir, onto the transdermal membrane, and to the skin of the patient.

This and other embodiments can include one or more of the following features. The method can further include alternately rotating the cam in a first direction and a second directions so as to deliver sequential doses of the formulation. The method can further include rotating the cam in a same direction so as to deliver sequential doses of formulation. The method can further include engaging a second tooth of the plurality of teeth with the second camming surface so as to stop the formulation from flowing out of the reservoir.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2D show operation of the rotational plunger of the delivery device of FIGS. 1A-1C.

FIGS. 3A-3E show a transdermal delivery device with a linear plunger.

FIGS. 5A-5B show a close-up of the valve system of the delivery device of FIGS. 3A-3E.

FIGS. 6A-6D show a transdermal delivery system with a storage latch.

DETAILED DESCRIPTION

The present application discloses devices and methods for transdermal delivery of a formulation, e.g., a bioactive agent.

Figure 1A:
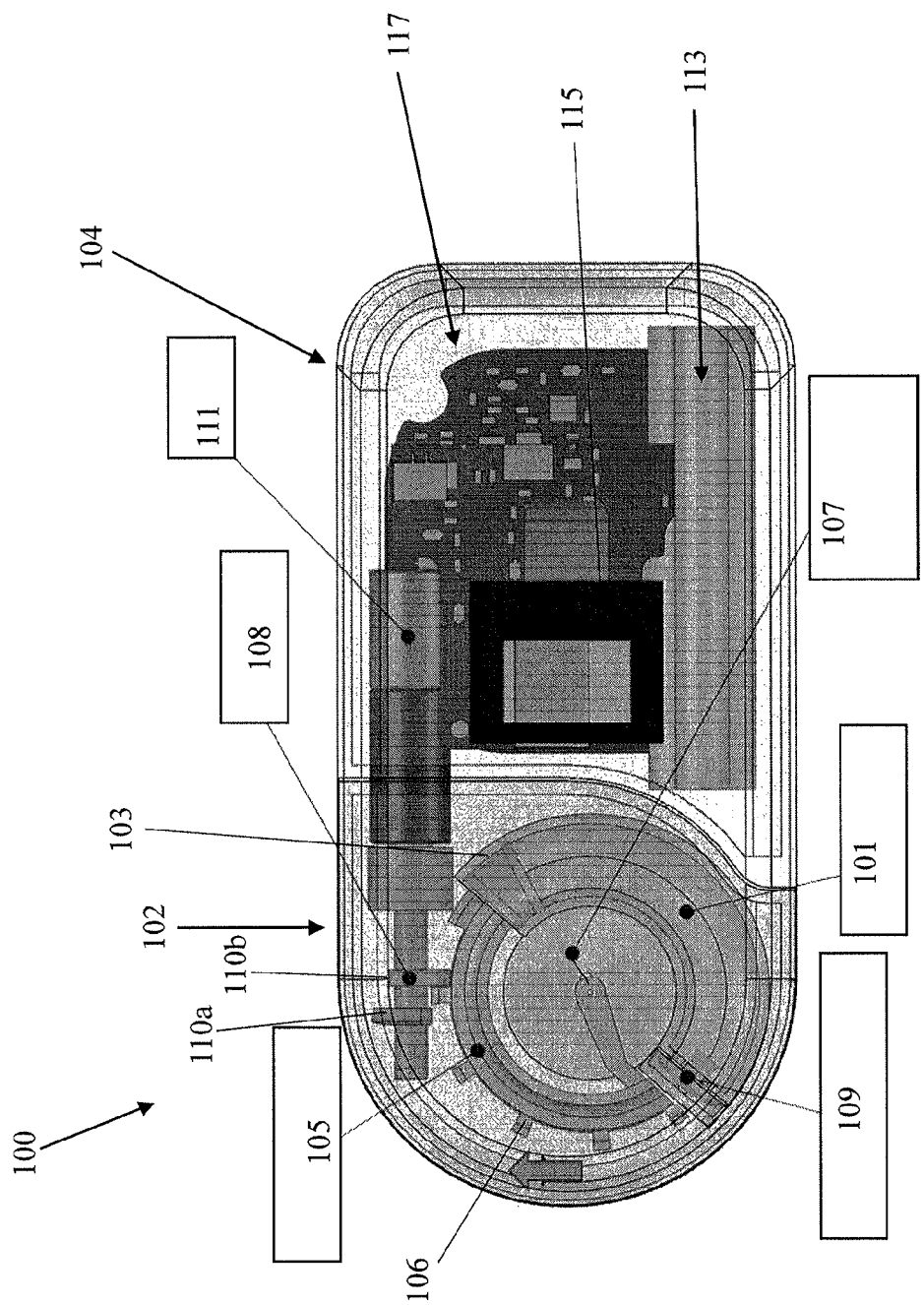
FIGS. 1A-1C show a transdermal delivery device with a rotational plunger.
Figure 1B:
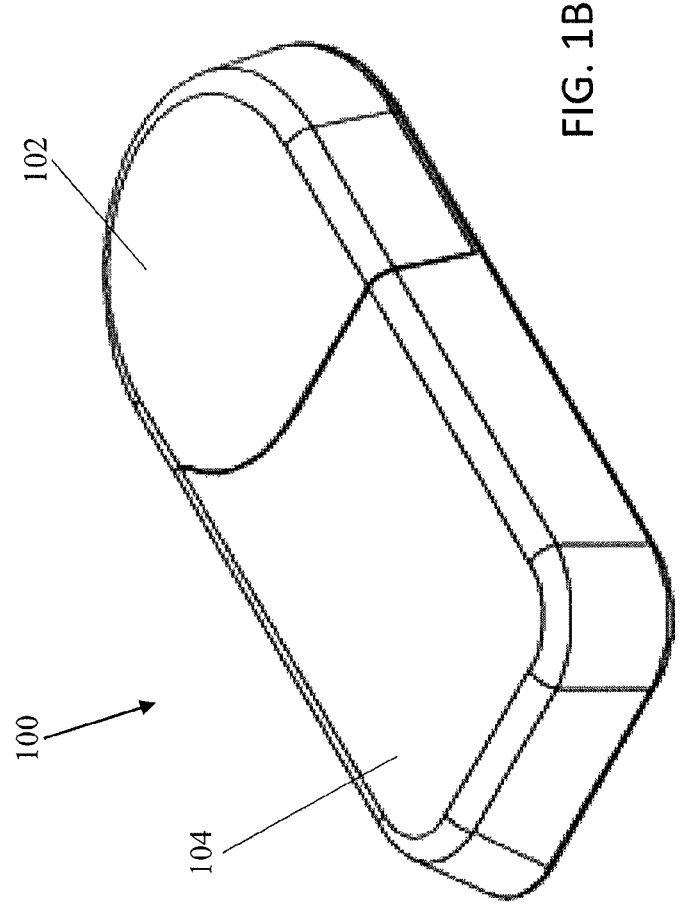
Figure 1C:
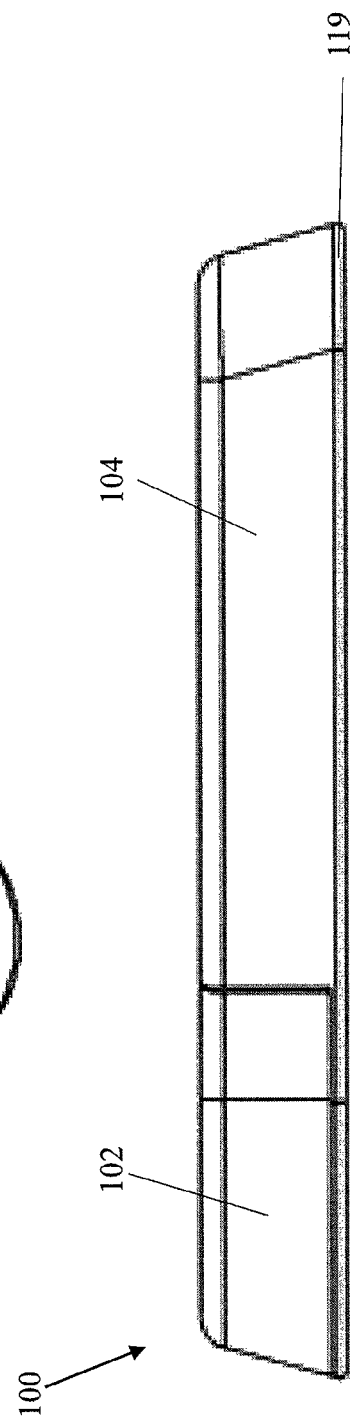
Figure 3A:
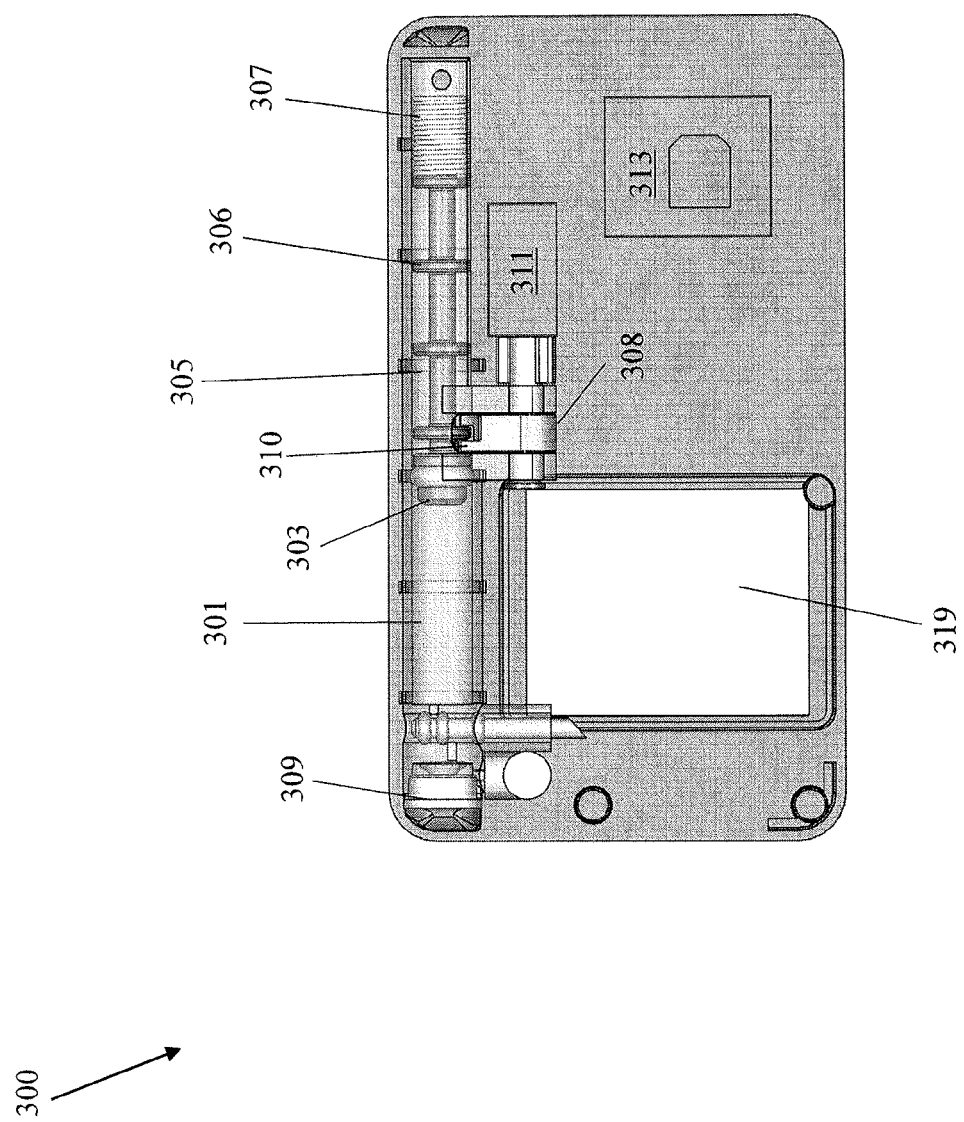
Figure 3D:
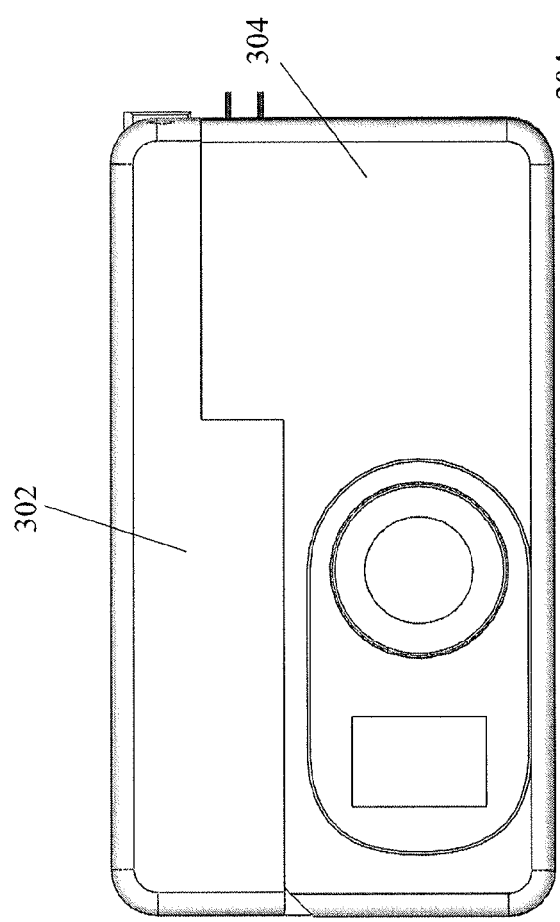
Figure 3E:
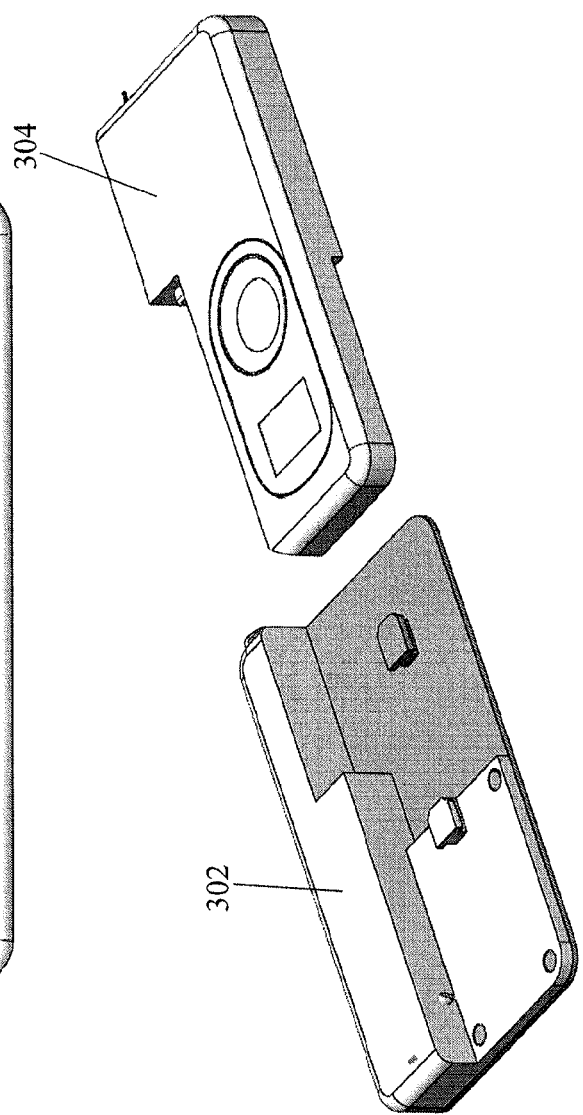

An exemplary transdermal drug delivery device is shown in FIGS. 1A-1C. The delivery device 100 includes a reservoir 101 having a semi-annular (i.e., curved) shape. Further, a rotational plunger including a piston 103 and curved control rod 105 (or drive wheel) can extend at least partially within the reservoir 101. A torsion spring 107 can bias the control rod 105 and piston 103 towards the reservoir 101. The control rod 105 can include a plurality of teeth 106 thereon. Further, a rotatable cam 108 (or cam lock) having two cam surfaces 110a, 110b can be positioned such that the cam surfaces 110a,b can engage with the teeth 106 of the control rod 105. The cam surfaces 110a,b can be semicircular and can be circumferentially offset relative to one another (e.g., such that there is no circumferential overlap between the two surfaces 110a,b). A valve 109, such as an umbrella valve, can be positioned at the distal end of the reservoir 101 and can prevent fluid from exiting the reservoir 101 until activated by the piston 103. Further, a motor 111 can be connected to the cam 108 so as to rotate the cam 108. The device 100 can further include a printed circuit board (PCB) 117 to control the delivery of fluid as well as a power source, such as a battery 113, and a display 115. A transdermal membrane 119 can be fluidically connected to the reservoir 101 so as to transfer formulation to the skin of the patient during use of the device 100.

The rotational plunger (including the control rod 105 and piston 103) can exert a force on the formulation in the reservoir 101 to expel a dose of the formulation from the reservoir 101. The valve 109, which can be an umbrella or check valve, can be used to prevent leakage of fluid from the reservoir 101 in between doses. The plurality of teeth 106 of the control rod 105 can be contacted by the cam surfaces 110a, 110b of the cam to prevent the piston 103 from moving distally (i.e., further into the reservoir 101) when not activated. The rotational plunger, including the control rod 105 and the piston 103, can be biased distally (i.e., towards the formulation in the reservoir 101) by the compressed torsion spring 107. When the cam surfaces 110a, 110b from the cam 108 no longer restrain the rotating plunger (i.e., when the cam surfaces 110a,b are rotated by the motor 111 so as to release one of the teeth 106 of the control rod 105), the plunger advances distally. Referring to FIG. 1A, as the plunger rotates clockwise (distally into the reservoir 101), a force can be applied to the formulation in the reservoir 101 to expel the solution through the valve 109 and onto the transdermal membrane 119. The next tooth 106 then advances distally and is caught on one of the cam surfaces 110a,b to stop the rotating plunger from moving any further.

The teeth 106 on the control rod 105 can be spaced such that the desired amount of drug is delivered from the reservoir 101. The teeth 106 can be spaced evenly or can have a non-uniform spacing corresponding to the desired drug delivery profile. Further, in some embodiments, a spacing between the teeth 106 can be equivalent to a spacing between the two cam surfaces 110a,b.

In some embodiments, the drug delivery device 100 can include a separable cartridge 102 and control unit 104. The cartridge 102 can, for example, be disposable while the control unit 104 can, for example, be reusable. The cartridge 102 can include the reservoir 101, control rod 105, piston 103, cam 108, spring 107, valve 109, and membrane 119. The control unit 104 can include the motor 111, PCB 117, display 115, and power source 113. In some embodiments, the control unit 104 can further include a user interface.

FIGS. 2A-2D illustrate the operation of the rotational plunger (including control rod 105 and plunger 103) and cam 108 to expel fluid from the reservoir 101. As shown in FIG. 2A, the piston 103 can start at a proximal position (e.g., be positioned at the proximal end of the reservoir 101). In this position, the distal cam surface 110a can engage with a first tooth 106a to prevent the torsion spring 107 from moving the control rod 105 and piston 103 distally (i.e. into the reservoir 101). At FIG. 2B, the cam 108 can be rotated such that the distal cam surface 110a disengages from the first tooth 106a. As show in FIG. 2C, the torsion spring 107 can rotate and/or push the control rod 105 and piston 103 into the reservoir 101 to expel a dose of fluid formulation from the reservoir 101. The dose can end (formulation can stop flowing from the reservoir 101) as the second tooth 106b engages with the proximal cam surface 110b. As shown at FIG. 2D, the cam 108 can then be rotated again such that the proximal cam surface 110b disengages from the second tooth 106b. The cam rod 105 and piston 103 can thus rotate and/or move distally to expel fluid formulation from the reservoir 101 until the second tooth 106b engages with the distal cam surface 110a. The process can be continued (e.g., the cam 108 can be further rotated such that the teeth 106 and cam surfaces 110 sequentially engage) to dispel additional doses.

In some embodiments, the cam 108 can be configured to rotate in opposite directions to engage the first and second surfaces 110a,b with the teeth 106 sequentially. In other embodiments, the cam 108 can be configured to rotate in a single direction (e.g., a half rotation) repeatedly to engage the first and second surfaces 110a,b with the teeth 106 sequentially.

The range of motion of the piston 105 for each rotation of the cam 108 can be controlled by varying the spacing between the teeth 106. This feature can be utilized for customizing the dose to be delivered from the device. In one example of non-uniform spacing, the teeth can have a spacing corresponding to delivering bolus volumes of 155 μL, 125 μL, and 80 μL. For a plunger with an internal bore diameter of 4.85 mm, the teeth spacing can be 8.39 mm (155 μL), 6.77 (125 μL) mm, and 4.33 mm (80 μL). The teeth spacing can be adjusted, for example, based on the desired bolus volume and plunger geometry. The drug delivery profile can correspond to a circadian rhythm or a biosynchronous pattern of a patient using the transdermal drug delivery device. Examples of circadian rhythm or a biosynchronous drug delivery profile that can be used with the devices described herein are disclosed in US 2015/0283367 and U.S. Pat. No. 8,741,336, the disclosures of each of which are incorporated by reference in its entirety.

Another exemplary transdermal delivery device is shown in FIGS. 3A-3E. The device 300 is similar to 100 and can include similar features to those described above with respect to device 100. In contrast to claim 100, however, the reservoir 301 and plunger (including rod 305 and piston 303) are substantially linear. The transdermal delivery device 300 thus includes a reservoir 301 having a substantially straight or linear shape. Further, a linear plunger including a piston 303 and straight control rod 305 can extend at least partially within the reservoir 301. A compressed spring 307 can bias the control rod 305 and piston 303 towards the reservoir 301. The control rod 305 can include a plurality of teeth 306 thereon. Further, a rotatable cam 308 (or cam lock) having two cam surfaces 310 can be positioned such that the cam surfaces 310 can engage with the teeth 306 of the control rod 305. The cam surfaces 310 can be semi-circular and can be circumferentially offset relative to one another (e.g., such that there is no circumferential overlap between the two surfaces 310). A valve 309, such as an umbrella valve, can be positioned at the distal end of the reservoir 301 and can prevent fluid from exiting the reservoir 301 until activated by the piston 303. Further, a motor 311 can be connected to the cam 308 so as to rotate the cam 308. The device 300 can further include a printed circuit board (PCB) 317 (see FIG. 3B) to control the delivery of fluid as well as a power source, such as a battery 313, as well as a display 315 and user interface 333 (see FIG. 3B). A transdermal membrane 319 can be fluidically connected to the reservoir 301 so as to transfer fluid to the skin of the patient during use of the device 300.

In some embodiments, the device 300 can include two parts, including a cartridge 302 (shown in FIG. 3C) and a control unit 304 (shown in FIG. 3B), as described with respect to device 100.

The spring 307 can have a compressed configuration such that a force is exerted on the linear plunger (e.g., rod 305 and piston 303). The cam 308, however, can prevent the piston 303 from moving into the reservoir 301 by engaging with the teeth 306 of the control rod 305. When the cam 308 is rotated, a cam surface 310 can disengage with a first tooth 306 on the linear rod 305 to allow the piston 303 to advance until a second tooth 306 on the linear control rod 305 engages with a second cam surface 310 of the cam 308. The advancement of the linear rod 305 and piston 303 pushes on the fluid formulation in the reservoir 301 to expel the formulation from the reservoir 301. The formulation can then travel to the transdermal membrane 319 for release to the skin.

Figure 4A:
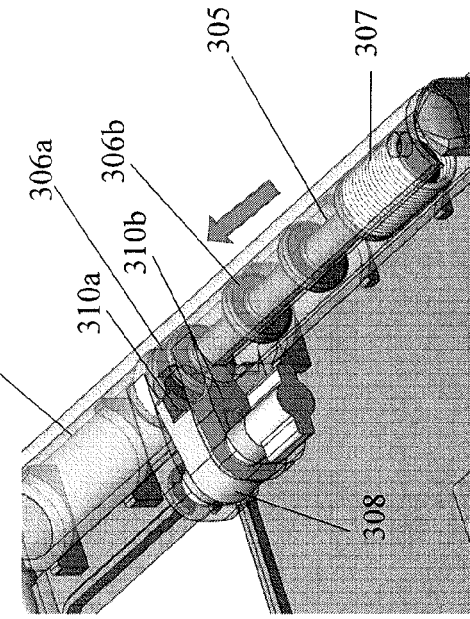
FIGS. 4A-4D show operation of the linear plunger of the delivery device of FIGS. 3A-3E.
Figure 4B:
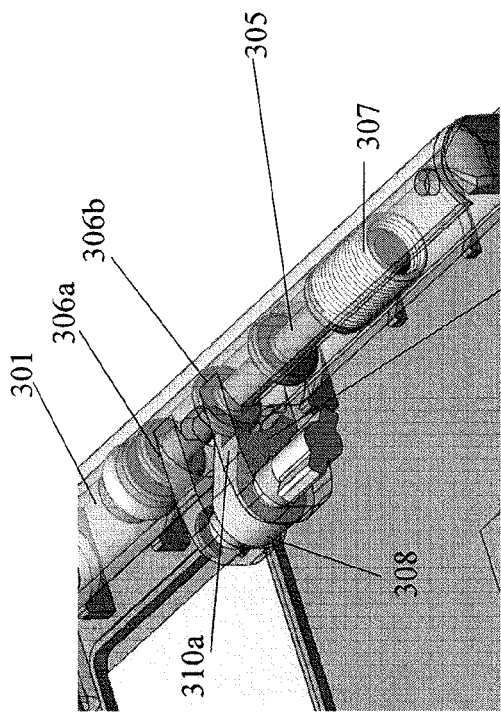
Figure 4C:
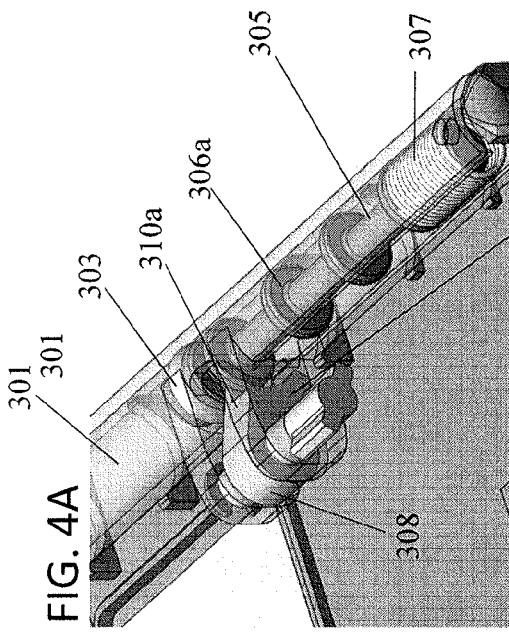
Figure 4D:
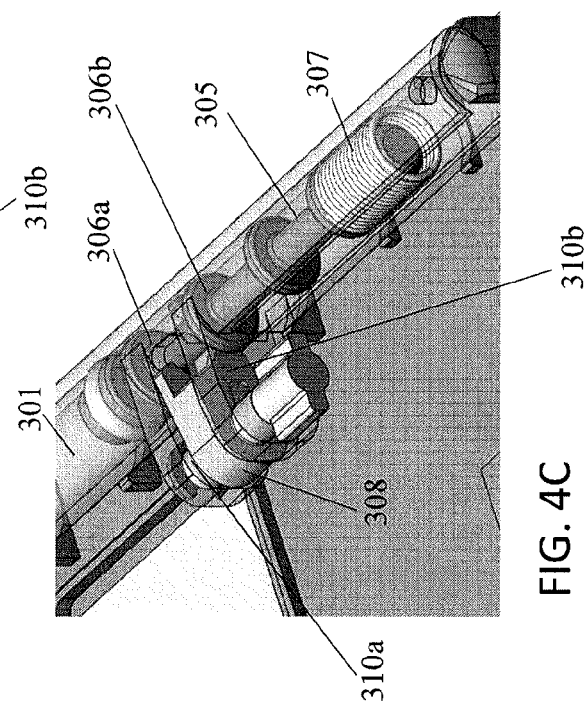

FIGS. 4A-4D illustrate the actuation of the device 300 in accordance with some embodiments. As shown in FIG. 4A, the piston 303 can start at a proximal position (e.g., be positioned at the proximal end of the reservoir 301). In this position, the distal cam surface 310a can engage with a first tooth 306a to prevent the spring 307 from moving the control rod 305 and piston 303 distally (i.e. linearly into the reservoir 301). At FIG. 4B, the cam 308 can be rotated such that the distal cam surface 310a disengages from the first tooth 306a. As show in FIG. 4C, the spring 307 can then push the control rod 305 and piston 303 into the reservoir 301 to expel a dose of fluid formulation from the reservoir 301. The dose can end as the second tooth 306b engages with the proximal cam surface 310b. As shown at FIG. 4D, the cam 308 can be rotated such that the proximal cam surface 310b disengages from the second tooth 306b. The cam rod 305 and piston 303 can thus move distally to expel fluid formulation from the reservoir 301 the second tooth 306b engages with the distal cam surface 310a. The process can be continued (e.g., the cam 308 can be further rotated such that the teeth 306 and cam surfaces 310 sequentially engage) to dispel additional doses.

Referring to FIGS. 5A-5B, in some embodiments, a pathway 555 can extend from the reservoir 501 to the transdermal membrane 519. Further, in some embodiments, a spool valve 557 can be used to prevent or minimize evaporative losses from the reservoir 501 during storage. The spool valve 557 can translate to allow the formulation to pass through the spool valve 557, valve 509, and the pathway 555 to the transdermal membrane 519. The spool valve 557 can reduce leakage or evaporative losses from the reservoir during extended storage conditions.

Referring to FIGS. 6A-6D, in some embodiments, a transdermal delivery system 600 similar to device 300 can have a storage latch 666 configured to hold the spring 607 away from the control rod 605 during storage. When the control unit 604 engages with the cartridge 602 (as shown from FIGS. 6B to 6C), the latch 666 can be pushed out of the way of the control rod 605 (by the control unit 604), allowing the control rod 605 to move freely. The latch 666 can thus advantageously help prevent fluid from accidentally be pushed out of the reservoir 601 during storage. Further, in some embodiments, the control unit 604 can push against the distal edge 699 of the control rod 605 (e.g., can move the control rod 2-3 mm) when the control unit 604 is inserted against the cartridge 602 to break the stiction of the control rod 605 and spring 607.

Figures 7A, 7B:
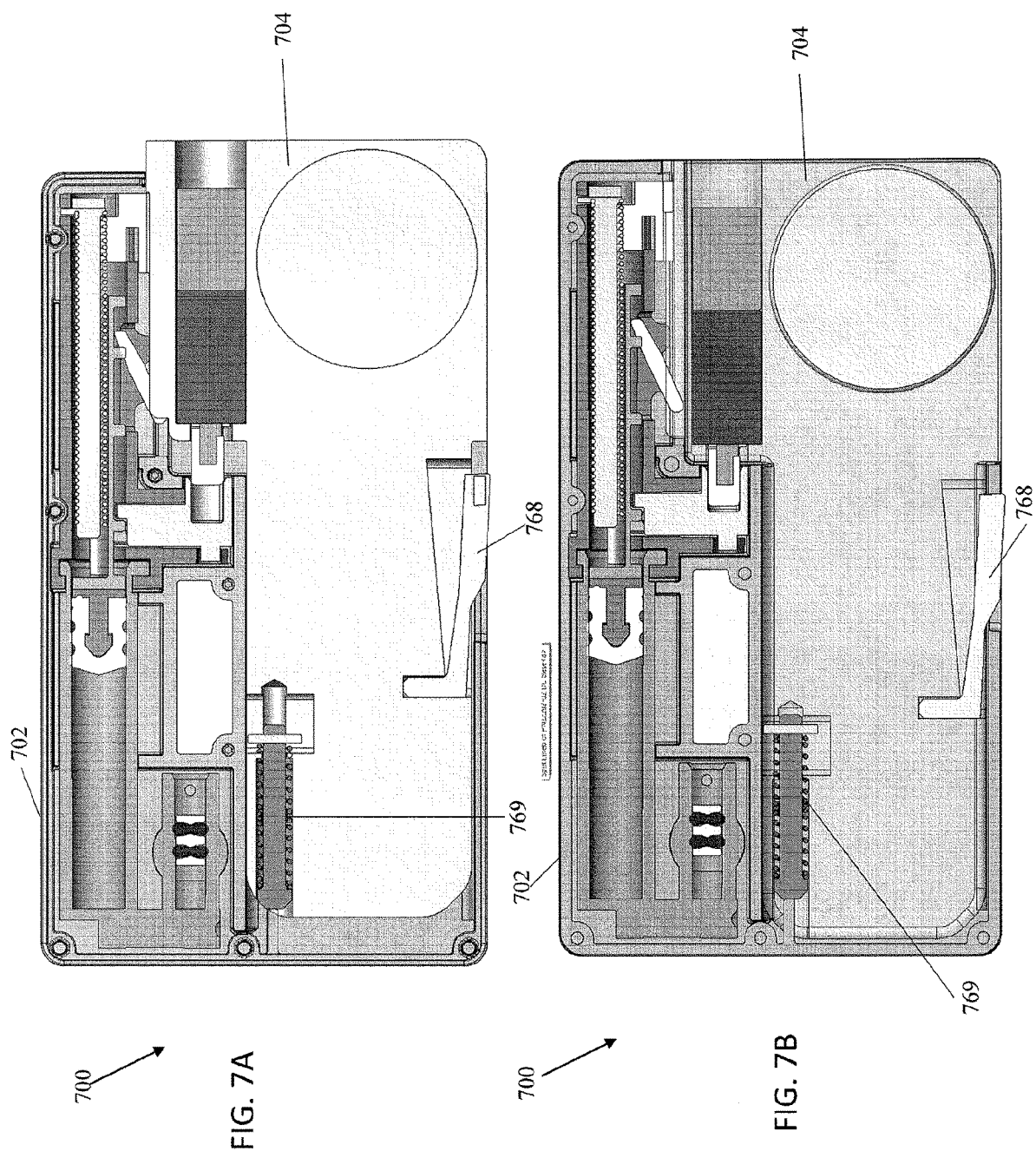
FIGS. 7A-7B show a transdermal delivery system with an ejection spring.

Additionally, in some embodiments, as shown in the device of FIGS. 7A-7B, an ejection spring 769 can be used to help push the control unit 704 and cartridge 702 apart when released (e.g., by release button 768).

The PCBs described herein can include a control unit, processor, wireless data transfer module, and any other electronics used to operate the device. The wireless data transfer module can wirelessly transmit data over a network and/or to and from a computer, such as a hand-held computer (e.g., a smartphone or tablet computer). A software application on the computer can be used to interact with the transdermal drug delivery devices described herein. In some embodiments, sensors can be included on the PCB, such as an accelerometer, temperature sensor, or humidity sensor.

The transdermal drug delivery devices described herein can have various plunger configurations and designs. The size and shape of the reservoir can be configured to work with the plunger configuration. As described above, in some embodiments the plunger and reservoir have a substantially linear configuration while in some embodiments, the plunger and reservoir have a semi-annular or curved configuration.

The transdermal drug delivery devices described herein can have a relatively small profile and volume. The length of the device can be 60-80 mm, such 70 mm, the width of the device can be 30-45 mm, such as 39 mm, and the thickness of the device 100 can be 6-12 mm, such as 9 mm. The volume of the transdermal drug delivery device 100 can be between 15 and 30 $cm^3$, such as about 25 $cm^3$.

The transdermal drug delivery devices described herein can enable the use of a only a small plunger spring. The use of a small spring reduces the complexity, size, and cost of the device. In some embodiments, the plunger spring is adapted to apply a force of about 12 N or less, such as ION or less, such as 5N or less, such as 3N or less to move the plunger. Where a torsion spring is used, the travel for the torsion spring can be less than about 200° of travel, such as 180° or less.

In some embodiments, a solenoid can be used to activate the cam. In some embodiments, the force used by the motor to actuate the cam is less than about 30 Nm.

In some embodiments, an adhesive can be used with the disposable part for adhering the transdermal drug delivery device to a skin of a patient.

The drug delivery devices described herein can include a transdermal membrane that contacts the wearer's skin. The formulation in the reservoir can be delivered in a controlled amount to the transdermal membrane. The transdermal membrane may be any appropriate material(s) or have any appropriate characteristics that can transfer the bioactive agent across the membrane. The transdermal membrane may be hydrophilic or hydrophobic. The transdermal membrane may have pores having a diameter from 0.010-0.01 μm (e.g., from 0.02 μm-0.05 μm, etc.). The membrane may have porosity over 20%-60% (e.g., from 30%-50%, from 45% to 50%, etc.). In a particular example, the membrane can be made of polypropylene, such as Celgard 2400 polypropylene (e.g., with a thickness around 25 μm such as between 1 μm and 100 μm, with a pore size around 0.043 such as from 0.005 to 0.2 μm, etc. may be used). The material for the transdermal membrane may be chosen, for example, based on the formulation or bioactive agent used or the length of treatment.

A variety of different formulations can be used with the systems described herein. In some embodiments, the formulation includes nicotine. For example, nicotine can be present in the formulation from about 0.5% to about 20% by volume, such as about 0.5% to about 10% by volume, such as about 0.5% to about 5% by volume, such as about 0.5% to about 3% by volume.

Other formulations that can be delivered by the devices described herein include the following drugs and combinations thereof, and modified forms of these drugs including but not limited to salt forms and combinations thereof: Acamprosate, Acetaminophen, Alfentanil, Allopurinol, Almotriptan, Alprazolam, Amitriptylinem, Amoxapine, Apomorphine, Aripiprazole, Armodafinil, Asenapine, Atomoxetine, Azelastine, Baclofen, Benzbromarone, Benzydamine, Brexpiprazole, Budesonide, Bupivacaine, Buprenorphine, Buprenorphine, Bupropion, Buspirone, Cabergoline, Capsaicin, Carbamazepine, Carbidopa, Carisprodol, Celecoxib, Citalopram, Clobazam, Clonazepam, Clonidine, Clopidogrel, Colchicine, Cyclobenzaprine, Dalteparin, Desvenlafaxine, Dexamfetamine, Dexmethylphenidate, Diazepam, Diclofenac, Disulfiram, Divalproex, Dolasetron, Doxepin, Dronabinol, Droxidopa, Duloxetine, Eletriptan, Entacapone, Escitalopram, Eslicarbazepine, Esomeprazole, Estradiol, Estrogen, Eszopiclone, Ethosuximide, Etodolac, Ezogabine, Febuxostat, Felbamate, Fenbufen, Fentanyl, Flunisolide, Fluorouracil, Fluoxetine, Fluticasone, Fluvoxamine, Formoterol, Fosphenytoin, Frovatriptan, Gabapentin, Granisetron, Guanfacine, Hydrocodone, Hydrocodone, Hydrocortisone, Hydromorphone, Hydroxyzine, *Hypericum* Extract, Ibuprofen, Indometacin, Ketorolac, Lacosamide, Lamotrigine, Levetiracetam, Levodopa, Levomilnacipran, Levosalbutamol, Lidocaine, Lisdexamfetamine, Lithium, Lorazepam, Lorcaserin, Losartan, Loxapine, Meclizine, Meloxicam, Metaxalone, Methylphenidate, Milnacipran, Mirtazapine, Modafinil, Morphine, Nabilone, Nadolol, Naloxone, Naltrexone, Naproxen, Naratriptan, Nedocromil, Nefazodone, Nitroglycerin, Olanzapine, Ondansetron, Orlistat, Oxaprozin, Oxcarbazepine, Oxybutynin, Oxycodone, Oxymorphone, Palonosetro, Pamidronate, Paroxetine, Perampanel, Phentermine, Phentolamine, Pramipexole, Prasugrel, Prazepam, Prednisone, Pregabalin, Procaine, Promethazine, Propofol, Quetiapine, Ramelteon, Rasagiline, Remifentanil, Risperidone, Rivastigmine, Rizatriptan, Ropinirole, Ropivacaine, Rotigotine, Rufinamide, Salbutamol, Scopolamine, Selegiline, Sertraline, Sodium Oxybate, Strontium, Sufentanil, Sumatriptan, Suvorexant, Tapentadol, Tasimelteon, Temazepam, Testosterone, Tetracaine, Theophylline, Tiagabine, Tiotropium, Tirofiban, Tolcapone, Topiramate, Tramadol, Trazodone, Triazolam, Trimipramine, Valproic acid, Venlafaxine, Vigabatrin, Vilazodone, Vortioxetine, Zaleplon, Zileuton, Ziprasidone, Zolmitriptan, Zolpidem, Norethisterone, Enalapril, Ethinyl Estradiol, Insulin, Memantine, Methamphetamine, Norelgestromine, Pergolide, Ramipril, Tecrine, Timolol, Tolterodine, and Zonisamide.

In some embodiments, the formulation used with the delivery devices described herein can include a bioactive agent (e.g., comprising one of the formulations described herein) and a solvent. In such cases, the transdermal membrane can be configured to minimize permeation of the solvent solution while permitting diffusion of a drug or other bioactive agent across the membrane and into contact with the skin. The solvent solution can be removed through a vapor permeable membrane.

In embodiments where the solvent is removed, the removed solvent can be collected in a solvent removal element. An example of a solvent removal element that can be used in the transdermal drug delivery devices described herein is disclosed in U.S. Pat. No. 8,673,346, the disclosure of which is incorporated by reference in its entirety. In some embodiments, the composition of the solvent can be designed and selected to optimize the diffusion of the drug or bioactive agent across the transdermal membrane. In some embodiments, the composition of the solvent can also be chosen in combination with the transdermal membrane to achieve the desired drug or bioactive agent delivery rate. In some embodiments, the solvent recovery element that includes an absorbent to receive and hold the solvent. The solvent recovery element can be part of the disposable part or cartridge. An absorbent for use with a transdermal patch as described herein may be an absorbent gel, blotting paper, paper, other polymer, silica gel or other material that readily soaks up or holds a fluid media such as a solvent liquid or vapor. The absorbent generally behaves as a physical sponge. The absorbent may be any structure or shape, such as a single piece or a plurality of pieces. The absorbent may be an amorphous material or a formed material, and may be a block, a layer, a sheet, a plurality of sheets, a plurality of particles and so on. A desiccant may be used instead or in addition to the absorbent.

The solvent for a bioactive agent may include a single component or multiple components, such as alcohol, water, or another solvent that readily vaporizes. One or more than one component may vaporize and be absorbed by absorbent. In some embodiments, the solvent solution includes water, alcohol, and a drug or bioactive agent. In some embodiments, the alcohol can be one or more of isopropanol, ethanol, and methanol. The solvent solution can also include one or more of a: surfactant, excipient, or other component intended to enhance permeation or decrease skin sensitivity or skin reaction. The solvent solution can have a ratio of water to alcohol of about 40:60 to about 60:40. The solvent solution can have a ratio of water to alcohol of about 45:55 to about 55:45. The solvent solution can have a ratio of water to alcohol of about 46:54 to about 54:46. The solvent solution can have a ratio of water to alcohol of about 47:53 to about 53:47. The solvent solution can have a ratio of water to alcohol of about 48:52 to about 52:48. The solvent solution can have a ratio of water to alcohol of about 49:51 to about 51:49.

In some embodiments, the formulation (e.g., nicotine or any of the other formulations described herein) used with the devices described herein can be provided for smoking cessation or to treat Parkinson's and other conditions.

The systems described herein can efficiently deliver substantially all of the formulation (e.g., at least 90%, at least 95%, at least 97%, at least 98%, or at least 99% of the formulation) across the transdermal membrane into contact with the wearer's skin.

The systems described herein can be configured to provide a single bolus or to provide a plurality of boluses (such as 2 or more, 3 or more, 4 or more, or 5 or more boluses).

Any feature or element described herein with respect to one embodiment can be combined with, or substituted for, any feature or element described with respect to another embodiment. Further, transdermal drug delivery systems are described in US 2016/0220798 titled "Drug Delivery Methods and Systems," the entirety of which is incorporated by reference herein in its entirety. Any feature or element described with respect to an embodiment herein can be combined with, or substituted for, any feature or element described in US 2016/0220798.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A transdermal drug delivery device comprising:
   a reservoir configured to hold a formulation therein;
   a transdermal membrane configured to allow the formulation from the reservoir to pass therethrough;
   a piston configured to move into the reservoir;
   a control rod attached to the piston, the control rod including a plurality of teeth thereon;
   a spring configured to apply force to the control rod in the direction of the reservoir; and
   a rotational cam having a first camming surface and a second camming surface, the first camming surface and the second camming surface configured to engage with the plurality of teeth, wherein the first and second camming surfaces are circumferentially offset from one another;
   wherein the rotational cam, when rotated, is configured to disengage the first camming surface from a first tooth of the plurality of teeth, thereby allowing the spring to advance the piston into the reservoir to expel the formulation onto the transdermal membrane.

2. The transdermal drug delivery device of claim 1, further comprising a motor configured to rotate the rotational cam.

3. The transdermal drug delivery device of claim 2, wherein the device comprises a first part that includes the reservoir, transdermal membrane, piston, control rod, spring, and rotational cam and a second part that includes the motor and a power source, the first and second parts configured to engage and disengage from one another.

4. The transdermal drug delivery device of claim 3, wherein the first part is disposable and the second part is reusable.

5. The transdermal drug delivery device of claim 3, wherein the first part further includes a storage latch configured to hold the spring away from the control rod during storage, the storage latch configured to release the spring when the first and second parts are engaged.

6. The transdermal drug delivery device of claim 1, wherein a spacing between the plurality of teeth on the control rod defines a teeth spacing pattern, and wherein the teeth spacing pattern corresponds to a drug delivery profile of the transdermal drug delivery device.

7. The transdermal drug delivery device of claim 6, wherein the drug delivery profile corresponds to a circadian rhythm or a bio-synchronous pattern of a patient using the transdermal drug delivery device.

8. The transdermal drug delivery device of claim 1, wherein the device is configured such that, after the first camming surface disengages from the first tooth and pushes the spring to push the control rod and piston into the reservoir, the second camming surface is configured to engage with a second tooth of the plurality of teeth to stop the piston from moving further into the reservoir.

9. The transdermal drug delivery device of claim 8, wherein the cam is rotatable in a first direction to cause the first camming surface to disengage with the first tooth and the second camming surface to engage with the second tooth, and wherein the cam is rotatable in a second direction to cause the second camming surface to disengage from the second tooth and cause the piston to move further into the reservoir to expel more of the formulation.

10. The transdermal drug delivery device of claim 8, wherein the cam is rotatable alternately in the first and second directions to allow sequential bolus deliveries of the formulation.

11. The transdermal drug delivery device of claim 8, wherein the cam is rotatable a first distance in a first direction to cause the first camming surface to disengage with the first tooth and the second camming surface to engage with the second tooth, and wherein the cam is rotatable a second distance in the first direction to cause the second camming surface to disengage from the second tooth and cause the piston to move further into the reservoir to expel more of the formulation.

12. The transdermal drug delivery device of claim 1, further comprising a valve along a pathway between the reservoir and the transdermal membrane.

13. The transdermal drug delivery device of claim 1, wherein the formulation is selected from the group consisting of: nicotine, Acamprosate, Acetaminophen, Alfentanil, Allopurinol, Almotriptan, Alprazolam, Amitriptylinem, Amoxapine, Apomorphine, Aripiprazole, Armodafinil, Asenapine, Atomoxetine, Azelastine, Baclofen, Benzbromarone, Benzydamine, Brexpiprazole, Budesonide, Bupivacaine, Buprenorphine, Buprenorphine, Bupropion, Buspirone, Cabergoline, Capsaicin, Carbamazepine, Carbidopa, Carisprodol, Celecoxib, Citalopram, Clobazam, Clonazepam, Clonidine, Clopidogrel, Colchicine, Cyclobenzaprine, Dalteparin, Desvenlafaxine, Dexamfetamine, Dexmethylphenidate, Diazepam, Diclofenac, Disulfiram, Divalproex, Dolasetron, Doxepin, Dronabinol, Droxidopa, Duloxetine, Eletriptan, Entacapone, Escitalopram, Eslicarbazepine, Esomeprazole, Estradiol, Estrogen, Eszopiclone, Ethosuximide, Etodolac, Ezogabine, Febuxostat, Felbamate, Fenbufen, Fentanyl, Flunisolide, Fluorouracil, Fluoxetine, Fluticasone, Fluvoxamine, Formoterol, Fosphenytoin, Frovatriptan, Gabapentin, Granisetron, Guanfacine, Hydrocodone, Hydrocodone, Hydrocortisone, Hydromorphone, Hydroxyzine, *Hypericum* Extract, Ibuprofen, Indometacin, Ketorolac, Lacosamide, Lamotrigine, Levetiracetam, Levodopa, Levomilnacipran, Levosalbutamol, Lidocaine, Lisdexamfetamine, Lithium, Lorazepam, Lorcaserin, Losartan, Loxapine, Meclizine, Meloxicam, Metaxalone, Methylphenidate, Milnacipran, Mirtazapine, Modafinil, Morphine, Nabilone, Nadolol, Naloxone, Naltrexone, Naproxen, Naratriptan, Nedocromil, Nefazodone, Nitroglycerin, Olanzapine, Ondansetron, Orlistat, Oxaprozin, Oxcarbazepine, Oxybutynin, Oxycodone, Oxymorphone, Palonosetro, Pamidronate, Paroxetine, Perampanel, Phentermine, Phentolamine, Pramipexole, Prasugrel, Prazepam, Prednisone, Pregabalin, Procaine, Promethazine, Propofol, Quetiapine, Ramelteon, Rasagiline, Remifentanil, Risperidone, Rivastigmine, Rizatriptan, Ropinirole, Ropivacaine, Rotigotine, Rufinamide, Salbutamol, Scopolamine, Selegiline, Sertraline, Sodium Oxybate, Strontium, Sufentanil, Sumatriptan, Suvorexant, Tapentadol, Tasimelteon, Temazepam, Testosterone, Tetracaine, Theophylline, Tiagabine, Tiotropium, Tirofiban, Tolcapone, Topiramate, Tramadol, Trazodone, Triazolam, Trimipramine, Valproic acid, Venlafaxine, Vigabatrin, Vilazodone, Vortioxetine, Zaleplon, Zileuton, Ziprasidone, Zolmitriptan, Zolpidem, Norethisterone, Enalapril, Ethinyl Estradiol, Insulin, Memantine, Methamphetamine, Norelgestromine, Pergolide, Ramipril, Tecrine, Timolol, Tolterodine, and Zonisamide.

14. The transdermal drug delivery device of any claim 1, further comprising an adhesive for adhering the transdermal drug delivery device to a skin of a patient.

15. A method of transdermal drug delivery, the method comprising:
  applying a transdermal delivery system to the skin of a patient, the transdermal delivery system including a reservoir, a transdermal membrane, a piston, a control rod having a plurality of teeth, and a rotational cam having first and second camming surfaces;
  rotating the cam such that the first camming surface moves from a first position that engages with a first tooth of the plurality of teeth to a second position that disengages with the first tooth such that the piston advances and pushes a dose of a formulation out of the reservoir, onto the transdermal membrane, and to the skin of the patient; and
  alternately rotating the cam in a first direction and a second directions so as to deliver sequential doses of the formulation.

16. The method of claim 15, further comprising rotating the cam in a same direction so as to deliver sequential doses of formulation.

17. The method of claim 15, further comprising engaging a second tooth of the plurality of teeth with the second camming surface so as to stop the formulation from flowing out of the reservoir.

* * * * *